US 10,918,888 B2

United States Patent
Ramezanzadeh Moghadam et al.

(10) Patent No.: US 10,918,888 B2
(45) Date of Patent: Feb. 16, 2021

(54) RADIATION THERAPY TREATMENT VERIFICATION WITH ELECTRONIC PORTAL IMAGING DEVICE TRANSIT IMAGES

(71) Applicant: Sun Nuclear Corporation, Melbourne, FL (US)

(72) Inventors: Amir Ramezanzadeh Moghadam, Melbourne, FL (US); Jeffrey M. Kapatoes, Melbourne, FL (US)

(73) Assignee: SUN NUCLEAR CORPORATION, Melbourne, FL (US)

( * ) Notice: Subject to any disclaimer, the term of this patent is extended or adjusted under 35 U.S.C. 154(b) by 222 days.

(21) Appl. No.: 15/908,538

(22) Filed: Feb. 28, 2018

(65) Prior Publication Data

US 2018/0243586 A1   Aug. 30, 2018

Related U.S. Application Data

(60) Provisional application No. 62/465,126, filed on Feb. 28, 2017.

(51) Int. Cl.
*A61N 5/10* (2006.01)
*G06N 3/02* (2006.01)
(Continued)

(52) U.S. Cl.
CPC ......... *A61N 5/1071* (2013.01); *A61N 5/1039* (2013.01); *A61N 5/1075* (2013.01);
(Continued)

(58) Field of Classification Search
CPC ................ A61N 5/1075; A61N 5/1071; A61N 2005/1054; A61N 5/1039;
(Continued)

(56) References Cited

U.S. PATENT DOCUMENTS

| 759,608 A | 5/1904 | Harper |
|---|---|---|
| 1,239,145 A | 9/1917 | Wantz |

(Continued)

FOREIGN PATENT DOCUMENTS

| CA | 2718408 | 9/2009 |
|---|---|---|
| DE | 102009039345 A1 | 3/2011 |

(Continued)

OTHER PUBLICATIONS

"Hi-Art,"; www.tomotherapy.com; TomoTherapy, Madison, WI; 2007; pp. 1-8.
(Continued)

*Primary Examiner* — Christine H Matthews
*Assistant Examiner* — Joshua Daryl D Lannu
(74) *Attorney, Agent, or Firm* — Pillsbury Winthrop Shaw Pittman LLP

(57) ABSTRACT

A method for radiation therapy treatment verification includes, acquiring treatment plan information from a radiation therapy system, patient image data, and transit image data received from an electronic portal imaging device during radiation therapy. The treatment plan information is divided into a plurality of segments. Predicted segment image data is determined utilizing a predicted image calculation algorithm and at least the patient image data and the treatment plan information. A predicted integrated image is determined through superposition of the predicted segment image data. Measured segment responses are determined from the transit image data utilizing the predicted segment image data and the predicted integrated image. The measured segment responses are converted to measured segment doses. A measured dose map having a sum of the measured segment doses is compared to a planned dose map based on the treatment plan information to assess radiation treatment delivery.

14 Claims, 7 Drawing Sheets

(51) Int. Cl.
  *G06N 5/02*          (2006.01)
  *G16H 20/40*         (2018.01)
(52) U.S. Cl.
  CPC .............. *G06N 3/02* (2013.01); *G06N 5/022* (2013.01); *G16H 20/40* (2018.01); *A61N 2005/1054* (2013.01); *A61N 2005/1074* (2013.01)
(58) Field of Classification Search
  CPC .. A61N 2005/1074; G06N 3/02; G06N 5/022; G16H 20/40
  See application file for complete search history.

(56) References Cited

U.S. PATENT DOCUMENTS

| | | | |
|---|---|---|---|
| 2,818,510 A | 12/1957 | Verse |
| 3,033,985 A | 5/1962 | Ben |
| 3,394,258 A | 7/1968 | Schleiger |
| 3,433,953 A | 3/1969 | Sweet |
| 3,665,762 A | 5/1972 | Domen |
| 3,783,251 A | 1/1974 | Pavkovich |
| 3,790,794 A | 2/1974 | Murray |
| 3,980,885 A | 9/1976 | Steward |
| 4,058,832 A | 11/1977 | Vagi |
| 4,063,097 A | 12/1977 | Barrett |
| 4,107,531 A | 8/1978 | Garratt |
| 4,157,472 A | 6/1979 | Barrett |
| 4,312,224 A | 1/1982 | Domen |
| 4,450,440 A | 5/1984 | White |
| 4,455,609 A | 6/1984 | Inamura |
| 4,613,754 A | 9/1986 | Vinegar |
| 4,729,099 A | 3/1988 | Iverson |
| 4,765,749 A | 8/1988 | Bourgade |
| 4,777,442 A | 10/1988 | Rosenthal |
| 4,887,287 A | 12/1989 | Cobben |
| 5,099,505 A | 3/1992 | Seppi |
| 5,160,337 A | 11/1992 | Cosman |
| 5,262,649 A | 11/1993 | Antonuk |
| 5,388,142 A | 2/1995 | Morris |
| 5,394,452 A | 2/1995 | Swerdloff |
| 5,596,653 A | 1/1997 | Kurokawa |
| 5,602,892 A | 2/1997 | Llacer |
| 5,621,214 A | 4/1997 | Sofield |
| 5,622,187 A | 4/1997 | Carol |
| 5,627,367 A | 5/1997 | Sofield |
| 5,635,709 A | 6/1997 | Sliski |
| 5,640,436 A | 6/1997 | Kawai |
| 5,661,310 A | 8/1997 | Jones |
| 5,704,890 A | 1/1998 | Bliss |
| 5,712,482 A | 1/1998 | Gaiser |
| 5,873,826 A | 2/1999 | Gono |
| 6,038,283 A | 3/2000 | Carol |
| 6,125,335 A | 9/2000 | Simon |
| 6,131,690 A | 10/2000 | Galando |
| 6,148,272 A | 11/2000 | Bergstrom |
| 6,175,761 B1 | 1/2001 | Frandsen |
| 6,257,552 B1 | 7/2001 | Crow |
| 6,261,219 B1 | 7/2001 | Meloul |
| 6,301,329 B1 | 10/2001 | Surridge |
| 6,322,249 B1 | 11/2001 | Wofford |
| 6,345,114 B1 | 2/2002 | Mackie |
| 6,364,529 B1 | 4/2002 | Dawson |
| 6,398,710 B1 | 6/2002 | Ishikawa |
| 6,516,046 B1 | 2/2003 | Froehlich |
| 6,535,574 B1 | 3/2003 | Collins |
| 6,535,756 B1 | 3/2003 | Simon |
| 6,552,347 B1 | 4/2003 | Dimcovski |
| 6,560,311 B1 | 5/2003 | Shepard |
| 6,594,336 B2 | 7/2003 | Nishizawa |
| 6,609,626 B2 | 8/2003 | Young |
| 6,609,826 B1 | 8/2003 | Fujii |
| 6,626,569 B2 | 9/2003 | Reinstein |
| 6,636,622 B2 | 10/2003 | Mackie |
| 6,648,503 B2 | 11/2003 | Tanaka |
| 6,712,508 B2 | 3/2004 | Nilsson |
| 6,788,759 B2 | 9/2004 | Op De Beek |
| 6,799,068 B1 | 9/2004 | Hartmann |
| 6,810,107 B2 | 10/2004 | Steinberg |
| 6,810,108 B2 | 10/2004 | Clark |
| 6,833,707 B1 | 12/2004 | Dahn |
| 6,839,404 B2 | 1/2005 | Clark |
| 6,853,702 B2 | 2/2005 | Renner |
| 6,888,919 B2 | 5/2005 | Graf |
| 6,904,119 B2 | 6/2005 | Oikawa |
| 6,904,125 B2 | 6/2005 | Van Dyk |
| 6,904,162 B2 | 6/2005 | Robar |
| 6,974,254 B2 | 12/2005 | Paliwal |
| 6,990,368 B2 | 1/2006 | Simon |
| 6,992,309 B1 | 1/2006 | Petry |
| 7,016,454 B2 | 3/2006 | Warnberg |
| 7,065,812 B2 | 6/2006 | Newkirk |
| 7,076,023 B2 | 7/2006 | Ghelmansarai |
| 7,098,463 B2 | 8/2006 | Adamovics |
| 7,116,749 B2 | 10/2006 | Besson |
| 7,127,028 B2 | 10/2006 | Sendai |
| 7,127,030 B2 | 10/2006 | Tamegai |
| 7,142,634 B2 | 11/2006 | Engler |
| 7,193,220 B1 | 3/2007 | Navarro |
| 7,221,733 B1 | 5/2007 | Takai |
| 7,233,688 B2 | 6/2007 | Ritt |
| 7,234,355 B2 | 6/2007 | Dewangan |
| 7,298,820 B2 | 11/2007 | Nelson |
| 7,339,159 B2 | 3/2008 | Juh |
| 7,349,523 B2 | 3/2008 | Jenkins |
| 7,352,840 B1 | 4/2008 | Nagarkar |
| 7,371,007 B2 | 5/2008 | Nilsson |
| 7,386,089 B2 | 6/2008 | Endo |
| 7,420,160 B2 | 9/2008 | Delaperriere |
| 7,453,976 B1 | 11/2008 | Yin |
| 7,471,765 B2 | 12/2008 | Jaffray |
| 7,515,681 B2 | 4/2009 | Ebstein |
| 7,579,608 B2 | 8/2009 | Takahashi |
| 7,605,365 B2 | 10/2009 | Chen |
| 7,636,419 B1 | 12/2009 | Nelson |
| 7,668,292 B1 | 2/2010 | Bose |
| 7,734,010 B2 | 6/2010 | Otto |
| 7,750,311 B2 | 7/2010 | Daghighian |
| 7,766,903 B2 | 8/2010 | Blumenkranz |
| 7,773,723 B2 | 8/2010 | Nord |
| 7,778,383 B2 | 8/2010 | Koehler |
| 7,778,392 B1 | 8/2010 | Berman |
| 7,778,680 B2 | 8/2010 | Goode, Jr. |
| 7,782,998 B2 | 8/2010 | Langan |
| 7,945,022 B2 | 5/2011 | Nelms |
| 8,044,359 B2 | 10/2011 | Simon |
| 8,093,549 B2 | 1/2012 | Navarro |
| 8,130,905 B1 | 3/2012 | Nelms |
| 8,136,773 B2 | 3/2012 | Schmutzer |
| 8,147,139 B2 | 4/2012 | Papaioannou |
| 8,218,718 B1 | 7/2012 | Van Herk |
| 8,235,530 B2 | 8/2012 | Maad |
| 8,242,458 B2 | 8/2012 | Rinecker |
| 8,321,179 B2 | 11/2012 | Simon |
| 8,325,878 B2 | 12/2012 | McNutt |
| 8,430,564 B2 | 4/2013 | Simmons |
| 8,457,713 B2 | 6/2013 | Kagermeier |
| 8,474,794 B2 | 7/2013 | Liljedahl |
| 8,536,547 B2 | 9/2013 | Maurer |
| 8,541,756 B1 | 9/2013 | Treas |
| 8,605,857 B1 | 12/2013 | Renner |
| 8,632,448 B1 | 1/2014 | Schulte |
| 8,726,814 B1 | 5/2014 | Matteo |
| 8,794,899 B2 | 8/2014 | Cozza |
| 8,833,709 B2 | 9/2014 | Weng |
| 8,840,304 B2 | 9/2014 | Perez Zarate |
| 8,840,340 B2 | 9/2014 | Eisenhower |
| 8,874,385 B2 | 10/2014 | Takayanagi |
| 8,927,921 B1 | 1/2015 | Nelms |
| 9,050,460 B2 | 6/2015 | Hildreth |
| 9,097,384 B1 | 8/2015 | Simon |
| 9,463,336 B2 | 10/2016 | Nelms |
| 9,480,861 B2 | 11/2016 | Kapatoes |
| 9,561,388 B2 | 2/2017 | Hildreth |

(56) References Cited

U.S. PATENT DOCUMENTS

| | | |
|---|---|---|
| 9,586,060 B2 | 3/2017 | Seuntjens |
| 9,750,955 B2 | 9/2017 | McNutt |
| 9,895,557 B2 | 2/2018 | Seuntjens |
| 2001/0042841 A1 | 11/2001 | Lyons |
| 2002/0077545 A1 | 6/2002 | Takahashi |
| 2002/0080912 A1 | 6/2002 | Mackie |
| 2003/0043879 A1 | 3/2003 | Tanaka |
| 2003/0043960 A1 | 3/2003 | Op De Beek |
| 2003/0138077 A1 | 7/2003 | Lee |
| 2003/0231740 A1 | 12/2003 | Paliwal |
| 2004/0066880 A1 | 4/2004 | Oikawa |
| 2004/0068182 A1 | 4/2004 | Misra |
| 2004/0096033 A1 | 5/2004 | Seppi |
| 2004/0113094 A1 | 6/2004 | Lyons |
| 2004/0120560 A1 | 6/2004 | Robar |
| 2004/0211917 A1 | 10/2004 | Adamovics |
| 2004/0228435 A1 | 11/2004 | Russell |
| 2004/0251419 A1 | 12/2004 | Nelson |
| 2005/0013406 A1 | 1/2005 | Dyk |
| 2005/0077459 A1 | 4/2005 | Engler |
| 2005/0111621 A1 | 5/2005 | Riker |
| 2006/0002519 A1 | 1/2006 | Jenkins |
| 2006/0033044 A1 | 2/2006 | Gentry |
| 2006/0184124 A1 | 8/2006 | Cowan |
| 2006/0203964 A1 | 9/2006 | Nyholm |
| 2006/0203967 A1 | 9/2006 | Nilsson |
| 2006/0266951 A1 | 11/2006 | Fritsch |
| 2007/0041497 A1 | 2/2007 | Schnarr |
| 2007/0041499 A1 | 2/2007 | Lu |
| 2007/0071169 A1 | 3/2007 | Yeo |
| 2007/0081629 A1 | 4/2007 | Yin |
| 2007/0086577 A1 | 4/2007 | Kobayashi |
| 2007/0195930 A1 | 8/2007 | Kapatoes |
| 2008/0031406 A1 | 2/2008 | Yan |
| 2008/0049896 A1 | 2/2008 | Kuduvalli |
| 2008/0049898 A1 | 2/2008 | Romesberg, III |
| 2008/0091388 A1 | 4/2008 | Failla |
| 2008/0103834 A1 | 5/2008 | Reiner |
| 2008/0118137 A1 | 5/2008 | Chen |
| 2008/0260368 A1 | 10/2008 | Chang |
| 2008/0292055 A1 | 11/2008 | Boone |
| 2009/0003512 A1 | 1/2009 | Pouliot |
| 2009/0067576 A1 | 3/2009 | Maltz |
| 2009/0090870 A1 | 4/2009 | Ahnesjo |
| 2009/0175418 A1 | 7/2009 | Sakurai |
| 2009/0217999 A1 | 9/2009 | Becker |
| 2009/0227841 A1 | 9/2009 | Miyako |
| 2009/0250618 A1 | 10/2009 | Simon |
| 2009/0252292 A1 | 10/2009 | Simon |
| 2010/0008467 A1 | 1/2010 | Dussault |
| 2011/0022360 A1 | 1/2011 | Simon |
| 2011/0051893 A1 | 3/2011 | McNutt |
| 2011/0085716 A1 | 4/2011 | Chefd Hotel |
| 2011/0096906 A1 | 4/2011 | Langeveld |
| 2011/0158386 A1 | 6/2011 | Payne |
| 2011/0210258 A1 | 9/2011 | Black |
| 2011/0248188 A1 | 10/2011 | Brusasco |
| 2011/0278444 A1 | 11/2011 | Navarro |
| 2011/0306864 A1 | 12/2011 | Zarate |
| 2012/0014618 A1 | 1/2012 | Sun |
| 2012/0025105 A1 | 2/2012 | Brown |
| 2012/0292517 A1 | 11/2012 | Izaguirre |
| 2012/0305793 A1 | 12/2012 | Schiefer |
| 2012/0326057 A1 | 12/2012 | Remeijer |
| 2013/0048883 A1 | 2/2013 | Simon |
| 2013/0303902 A1 | 11/2013 | Smith |
| 2014/0016754 A1 | 1/2014 | Sugiyama |
| 2014/0064445 A1 | 3/2014 | Adler |
| 2014/0073834 A1 | 3/2014 | Hildreth |
| 2014/0094642 A1 | 4/2014 | Fuji |
| 2014/0105355 A1 | 4/2014 | Toimela |
| 2014/0263990 A1 | 9/2014 | Kawrykow |
| 2015/0080634 A1 | 3/2015 | Huber |
| 2015/0087879 A1 | 3/2015 | Nelms |
| 2015/0124930 A1* | 5/2015 | Verhaegen ........... A61N 5/1031 378/62 |
| 2015/0238778 A1 | 8/2015 | Hildreth |
| 2015/0283403 A1 | 10/2015 | Kapatoes |
| 2015/0309193 A1 | 10/2015 | Kozelka |
| 2015/0352376 A1 | 12/2015 | Wiggers |
| 2016/0067479 A1 | 3/2016 | Marcovecchio |
| 2016/0136460 A1* | 5/2016 | Baltes ................. A61N 5/1045 378/165 |
| 2016/0166857 A1 | 6/2016 | Nelms |
| 2016/0287906 A1* | 10/2016 | Nord ...................... A61N 5/103 |
| 2016/0310762 A1 | 10/2016 | Ramezanzadeh Moghadam |
| 2017/0021194 A1 | 1/2017 | Nelms |
| 2017/0177812 A1* | 6/2017 | Sjolund ................ G16H 20/40 |
| 2017/0274225 A1 | 9/2017 | Baecklund |
| 2018/0185672 A1 | 7/2018 | Ramezanzadeh Moghadam |

FOREIGN PATENT DOCUMENTS

| | | |
|---|---|---|
| EP | 1060726 | 12/2000 |
| EP | 1060726 B1 | 6/2004 |
| EP | 2016445 | 1/2009 |
| EP | 2078537 A1 | 7/2009 |
| EP | 2117649 A2 | 11/2009 |
| EP | 2186542 | 5/2010 |
| EP | 2457237 | 5/2012 |
| EP | 2708919 A2 | 3/2014 |
| EP | 2865417 | 4/2015 |
| EP | 2904974 | 8/2015 |
| EP | 3074088 | 10/2016 |
| EP | 3075417 | 10/2016 |
| JP | 05154209 | 6/1993 |
| JP | 2003310590 A | 11/2003 |
| JP | 2008105882 | 5/2008 |
| JP | 2010215428 | 9/2010 |
| JP | 2010234521 | 10/2010 |
| WO | 2006138513 | 12/2006 |
| WO | 2008013956 | 1/2008 |
| WO | 2009114669 | 9/2009 |
| WO | 2009120494 | 10/2009 |
| WO | 2009137794 | 11/2009 |
| WO | 2011011471 | 1/2011 |
| WO | 2012053440 | 4/2012 |
| WO | 2013049839 | 4/2013 |
| WO | 2013177677 | 12/2013 |
| WO | 2015024360 | 2/2015 |
| WO | 2015073899 | 5/2015 |
| WO | 2016172352 | 10/2016 |

OTHER PUBLICATIONS

"Rapid Arc"; Varian Medical Systems, Inc., Palo Alto, CA; www.varian.com; 2007; pp. 1-8.

"VMAT"; Elekta,Ltd., Crawley UK; Document No. 4513 3710770; Oct. 8, 2008.

"Waterphantom Dosimetry"; Medical Physics, vol. 3, May/Jun. 1976; pp. 189.

Ahnesjo et al. Phys. Med. Biol. 44, R99-R155 1999.

Ahnesjo et al., Acta. Oncol., 26, 49-56, 1987.

Ahnesjo, Med. Phys. 16, 577-92, 1989.

Albers et al., CRC HAndbook of Chemistry and Physics, 87th Ed., Edited by R.C. Weast (CRC, Cleveland, 1976. pp. F-11, D-171, E-6.

Almond et al. In "AAPM TG-51 Protocol for Clinical Reference Dosimetry of Hign Energy Photon and Electron Beams" (Med. Phys. VI, 26, pp. 1847-1870, 1999.

Amanatides et al., Eurographics '87, Conference Proceedings, 1987.

Aspen Aerogels, Pyrogel.RTM. 2250 Datasheet (Aspen Aerogels, Inc., Northborough, 2010).

Benedick Fraass; "Quality Assurance for Clinical Radiotherapy Treatment Planning," Med Phys., 25(10), Oct. 1998; pp. 1773-1829.

Berlyand et al., "Portable Calorimeter for Measuring Absorbed Doses of X-Rays and Electrons from Accelerators", translated from Izeriternaya Teknika, No. 11, Nov. 1991, pp. 56-58.

Boutillon in "Gap Correction for the Calorimetric Measurement of Absorbed Dose in Graphite with a 60Co Beam" (Phys. Med. Biol., vol. 34, pp. 1809-1821, 1989.

(56) References Cited

OTHER PUBLICATIONS

Brusasco, C, et al. 'A Dosimetry System for Fast Measurement of 3D Depth-dose Profiles in Charged-particle Tumor Therapy with Scanning Techniques.' Nuclear Instruments & Methods in Physics Research, Section—B: Beam Interactions With Materials and Atom 168.4 (2000): 578-92.
Cyberknife; Cyberknife Systems; "The Standard of Radiosurgery" by Accuracy, Sunnyvale, CA; 2009; pp. 1-6.
D.W.O. Rogers; "Montey Carlo Techniques in Radiotherapy,"; Physics in Canada, Medical Physics Special Issue, v. 58 #2; 2002; pp. 63-70.
Daures et al., "New Constant-Temperature Operating Mode for Graphite Calorimeter at LNE-LNHB", Physics in Medicine and Biology, vol. 50, 2005, No. pp. 4035-4052.
Daures et al., "Small section graphite calorimeter (CR10) at LNE-LNHB for measurement in small beams for IMRT", Metrologica, (Dec. 1, 2011), XP020229547.
Daures et al., "Small Section Graphite Calorimeter (GR-10) at LNE-LNHB for Measurements in Small Beams for IMRT Metrologia", vol. 49, No. 5, 2012, pp. S174-S178.
Domen et al., "A Heat-loss-Compensated Calori meter: Theory, Design, and Performance", Journal of Research of the National Bureau of Standards—A. Physics and Chemistry, vol. 78A, No. 5, Sep.-Oct. 1974, pp. 595-610.
Domen, "Absorbed Dose Water Calorimeter" (Med. Phys., vol. 7, pp. 157-159).
Duane et al., "An Absorbed Dose Calorimeter for IMRT Dosimetry", Metrologia, vol. 49, No. 5, 2012, pp. S168-S173.
EP2277353 Search Report dated Jul. 21, 2017.
EP2457237 Supplemental European Search Report and Written Opinion dated Mar. 8, 2017.
G.J. Kutcher; "Comprehensive AQ for Radiation Oncology Report;" AAPM Radiation Therapy Committee Task Group 40; Med. Phys., 21; Apr. 1994; pp. 581-618.
IAEA, TRS., "398. Absorbed Dose Determination in External Beam Radiotherapy: An International Code of Practice for Dosimetry based on Standards of Absorbed Dose to Water," Vienna International Atomic Energy Agency (2000).
Indra J. Das, Chee-Wai Cheng, Ronald J. Watt, Anders Ahnesjo, John Gibbons, X. Allen Li, Jessica Lowenstien, Raj K. Mitra, William E. Simon, Timothy C. Zhu; Accelerator Beam Data Commissioning Equiptment and Procedures; Report of the TG-106 of the Therapy Physics Committee of the Aapm; Med. Phys. 35(9), Sep. 2008; pp. 4186-4215.
J. Seuntjens and S. Duane, "Photon absorbed dose standards," Metrologia 46, S39-S58 (2009).
Joseph O. Deasy; "A Computational Environment for Radiotherapy Research," Med. Phys. 30, (5), May 2003; pp. 979-985.
Kawrakow et al. In "The EGSnrc Code System: Monte-Carlo Simulation of Electron and Photon Transport" (Canadian National Research Center, NRC Report PIRS-701, 2006.
Liu et al., Med. Phys. 24, 1729-1741, 1997.
Lu et al., Phys. Med. Biol. 50, 655-680, 2005.
Mackie et al., Med. Phys. 12, 188-196, 1985.
Mackie et al., Phys. Med. Biol. 33, 1-20, 1988.
Mackie et al., Use of Comp. In Rad. Ther., 107-110 1987.
MapCALC; www.sunnuclear.com; manufactured by Sun Nuclear Corp.; Melbourne, FL; 2009.
MapCheck and EPIDose; www.sunnuclear.com; manufactured by Sun Nuclear Corp.; Melbourne,FL; 2010.
Mathilda Van Zijtveld, Maaretn L.P. Dirkxa, Hans C.J. De Boera, and Ben J.M. Heijmen; "3D Dose Reconstruction for Clinical Evaluation of IMRT Pretreatment Verification with an EPID." Radiotherapy and Oncology, 82(2); Feb. 2007; pp. 201-201.
Mc Ewen at al., 'A Portable Calorimeter for Measuring Absorbed Dose in the Radiotherapy Clinic', Physics in Medicine and Biology, vol. 45, No. 12, Dec. 2000, pp. 3675-3691.
McDonald et al., "Portable Tissue Equivalent Calorimeter", Medical Physics, vol. 3, 2, Mar.-Apr. 1976, pp. 80-86.
McEwen et al., Portable Graphite Calorimeter for Measuring Absorbed Dose in the Radiotherapy Clinic.Standards and Codes of Practice in Medical Radiation Dosimetry,IAEA-CN-96-9P,2002, pp. 115-121.
Miller, "Polystyrene Calorimeter for Electron Beam Dose Measurements", Radiation Physics Chemistry vol. 46, No. 4-6, Aug. 1995, pp. 1243-1246.
Mohan et al., Med. Phys. 12, 592-597, 1985.
Myers et al., "Precision Adiabatic Gamma-Ray Calorimeter using Thermistor Thermometry", Review of Scientific Instruments, vol. 32, No. 9, Sep. 1961, pp. 1013-1015.
Nelms, Benjamin. "Variation in External Beam Treatment, Plan Quality: An Interinstitutional Study of Planners and Planning Systems." Practical Radiation Oncology 2.4 (2012): 296-305.
Nutbrown et. "Evaluation of Factors to Convert Absorbed Dose Calibrations in Graphite to Water for Mega-Voltage Photon Beams" (UK National Pysical Laboratory, NPL Report CIRM 37, 2000.
Ostrowsky et al., "The Construction of the Graphite Calorimeter GR9 at LNE-LNHB (Geometrical and technical considerations)", Report CEA-R-6184, 2008, 52 pages.
Otto, Med. Phys. 35, 310-317, 2008.
Owen et al "Correction for the Effect of the Gaps around the Core of an Absorbed Dose Graphite Calorimeter in High Energy Photon Radiation" (Phys. Med. Biol., vol. 36, pp. 1699-1704, 1991.
Palmans et al., "A Small-Body Portable Graphite Calorimeter for Dosimetry in Low-Energy Clinical Proton Beams", Physics in Medicine and Biology, vol. 49, No. 16, Aug. 2004, pp. 3737-3749.
Papanikolaou et al., Med. Phys. 20, 1327-1336, 1993.
PCT App. No. PCT/US2009/036775; International Preliminary Report on Patentability Chapter II and Written Opinion dated Sep. 12, 2010.
PCT App. No. PCT/US2009/036775; International Search Report dated Nov. 12, 2009.
PCT App. No. PCT/US2009/036917; International Preliminary Report on Chapter II Patentability dated Mar. 15, 2011.
PCT App. No. PCT/US2009/036917; International Search Report dated Sep. 17, 2009.
PCT App. No. PCT/US2009/036917; Written Opinion dated Sep. 12, 2010.
PCT App. No. PCT/US2009/043341; International Preliminary Report on Patentability Chapter I dated Nov. 9, 2010.
PCT App. No. PCT/US2009/043341; International Search Report dated Jan. 5, 2010.
PCT App. No. PCT/US2009/043341; Written Opinion of the International Search Authority dated Nov. 8, 2010.
PCT App. No. PCT/US2010/042680; International Preliminary Report on Patentability Chapter I dated Jan. 24, 2012.
PCT App. No. PCT/US2010/042680; International Search Report dated Jan. 27, 2011.
PCT App. No. PCT/US2010/042680; International Written Opinion dated Jan. 23, 2012.
PCT App. No. PCT/US2012/053440; International Preliminary Report on Patentability Chapter I dated Mar. 3, 2015.
PCT App. No. PCT/US2012/053440; International Search Report and Written Opinion dated Mar. 26, 2014.
PCT App. No. PCT/US2012/058345; International Preliminary Report on Patentability Chapter I dated Apr. 1, 2014.
PCT App. No. PCT/US2012/058345; International Search Report dated Apr. 17, 2013.
PCT App. No. PCT/US2012/058345; International Written Opinion of the International Search Authority dated Mar. 29, 2014.
PCT App. No. PCT/US2014/065808; International Preliminary Report on Patentability Chapter I dated May 17, 2016.
PCT App. No. PCT/US2014/065808; International Search Report and Written Opinion dated May 21, 2015.
PCT App. No. PCT/US2015/024360; International Preliminary Report on Patentability Chapter I dated Oct. 4, 2016.
PCT App. No. PCT/US2015/024360; International Search Report and Written Opinion dated Oct. 8, 2015.
PCT App. No. PCT/US2016/028664; International Preliminary Report on Patentability dated Nov. 2, 2017.
PCT App. No. PCT/US2017/062608; International Search Report and Written Opinion dated Feb. 22, 2018.

(56) References Cited

OTHER PUBLICATIONS

PCT/US2017/044472; International Search Report and Written Opinion of the International Searching Authority, or the Declaration dated Oct. 13, 2017.
Petree et al., "A Comparison of Absorbed Dose Determinations in Graphite by Cavity Ionization Measurements and by Calorimetry", Journal of Research of the National Bureau of Standards—C. Engineering and Instrumentation. vol. 71 C, No. 1, Jan.-Mar. 1967, pp. 19-27.
Picard et al., "Construction of an Absorbed-Dose Graphite Calorimeter", Report BIPM-09/01 May 2009, 12 pages.
R. Alfonso et al., 'A new formalism for reference dosimetry of small and nonstandard fields,' Med. Phys. 35, 5179-5186 (2008).
Renaud et al., "Development of a graphite probe calorimeter for absolute clinical dosimetry", Med. Phvs., (20130109), vol. 40, No. 2, p. 020701, XP012170941.
Robert M. Eisberg; "Fundamentals of Modern Physics," Chapter 9—Perturbation Theory; John Wiley & Sons; 1967; pp. 268-272.
Rogers, "The physics of AAPM's TG-51 protocol," in Clinical Dosimetry Measurements in Radiotherapy, Medical Physics Monograph No. 34, edited by D. W. O. Rogers and J. E. Cygler (Medical Physics Publishing, Madison, WI, 2009), pp. 239-298.
Ross et al. In "Water Calorimetry for Radiation Dosimetry" (Phys. Med. Biol., vol. 41, pp. 1-29).
S. Picard, D. T. Burns, and P. Roger, "Determination of the specific heat capacity of a graphite sample using absolute and differential methods," Metrologia 44, 294-302 (2007).
Sander et al., "NPL's new absorbed dose standard for the calibration of HDR 192Ir brachytherapy sources," Metrologia 49, S184-S188 (2012).
Seuntjens et al., Review of Calorimeter Based Absorbed Dose to Water Standards, Standards and Codes of Practice in Medical Radiation Dosimetry, IAEA-CN-96-3,2002 p. 37-66.
Stewart in "The Development of New Devices for Accurate Radiation Dose Measurement: A garded Liquid Ionization Chamber and an Electron Sealed Water Calorimeter" (Ph. D. Dissertation McGill University, 2007.
Sundara et al., "Graphite Calorimeter in Water and Calibration of Ionization Chambers in Dose to Water for 60Co Gamma Radiation", Medical Physics, vol. 7, No. 3, May-Jun. 1980, pp. 196-201.
T.R. McNutt, T.R. Mackie, P.J. Reckwerdt, B.R. Paliwal; "Analysis and Convergence of the Iterative Convolution/Superposition Dose Reconstruction Technique,"; Med. Phys. 24(9) Sep. 1997; pp. 1465-1476.
Williams, SIGGRAPH Comput. Graph. 17, 3, 1-11, 1983.
Witzani et al., "A Graphite Absorbed-Dose Calorimeter in the Quasi-Isothermal Mode of Operation", Metrologia, vol. 20, No. 3, 1984, pp. 73-79.
Y. Morishita et al., "A standard for absorbed dose rate to water in a 60Co field using a graphite calorimeter at the national metrology institute of Japan," Radiat. Prot. Dosim. 1-9 (2012) (published E-first Sep. 5, 2012).
Yan et al., Phys. Med. Biol. 42, 123-132, 1997.
Yu, Phys. Med. Biol. 40, 1435-1449, 1995.
McEwen et al.; "A portable calorimeter for measuring absorbed dose in radiotherapy clinic"; Dec. 2000; Phys. Med. Biol., vol. 45; pp. 3675-3691.
McDermott et al.; "Replacing Pretreatment Verification with In Vivo EPID Dosimetry for Prostate IMRT"; International Journal of Radiation: Oncology Biology Physics, Pergamon Press, USA, vol. 67, No. 5, Mar. 28, 2007, pp. 1568-1577, XP022101268, ISSN: 0360-3016, DOI: 10.1016/J.IJROBP.2006.11.047.
Nelms, Benjamin et al.; "Evalution of a Fast Method of EPID-based Dosimetry for Intensity-modulated Radiation Therapy"; Journal of Applied Clinical Medical Physics, Jan. 1, 2010, pp. 140-157, XP055476020.
PCT App. No. PCT/US2018/020320; International Search Report and Written Opinion dated Jul. 24, 2018.
Office Action dated Sep. 12, 2018 for U.S. Appl. No. 14/694,865 (pp. 1-7).
Linacre, J.K. , "Harwell Graphite Calorimeter", IAEA, vol. 47, 1970 (pp. 46-54.).
PCT App. No. PCT/US2018/020320; International Preliminary Report on Patentability Chapter I dated Sep. 12, 2019. pp. 1-11.
International Search Report and Written Opinion dated Oct. 2, 2020, PCT Application No. PCT/US2020/041458.

* cited by examiner

RADIATION THERAPY TREATMENT VERIFICATION WITH ELECTRONIC PORTAL IMAGING DEVICE TRANSIT IMAGES

CROSS-REFERENCE TO RELATED APPLICATIONS

The current application claims priority under 35 U.S.C. § 119(e) to U.S. Provisional Patent Application No. 62/465,126 filed Feb. 28, 2017 and entitled "RADIATION THERAPY TREATMENT VERIFICATION WITH ELECTRONIC PORTAL IMAGING DEVICE TRANSIT IMAGES," the contents of which is hereby incorporated by reference in their entirety.

BACKGROUND

Radiation therapy is used to treat cancerous tumors with ionizing radiation that kills the affected cancer cells. External beam radiotherapy is one method for delivering the ionizing radiation. In such therapy, a patient is placed on a couch and a radiotherapy beam generator (for example, a linear accelerator) is positioned to direct the ionizing radiation at the patient's tumor. One method for determining the proper positioning of the patient with respect to the beam is to use data from a radiation detector, for example an electronic portal imaging device (EPID). Images from an EPID depict the radiation exiting the patient, essentially providing an x-ray image that can be used to properly locate the patient with respect to the beam. Some modern EPID devices use a phosphor and an array of photosensors to detect radiation exiting the patient. Light from the phosphor is converted to an electrical signal and read by a computer to generate a mapping of the radiation pattern striking the phosphor.

SUMMARY

In a first aspect, a method for radiation therapy treatment verification includes, acquiring treatment plan information from a radiation therapy system, patient image data, and transit image data received from an electronic portal imaging device during radiation therapy. The treatment plan information is divided into a plurality of segments. Predicted segment image data is determined utilizing a predicted image calculation algorithm and at least the patient image data and the treatment plan information. A predicted integrated image is determined through superposition of the predicted segment image data. Measured segment responses are determined from the transit image data utilizing the predicted segment image data and the predicted integrated image. The measured segment responses are converted to measured segment doses. A measured dose map having a sum of the measured segment doses is compared to a planned dose map based on the treatment plan information to assess radiation treatment delivery.

In some variations, one or more of the following features can be added, in any combination.

A difference between the measured dose map and the planned dose map can be transmitted to a recipient device when the planned dose map corresponds to a sum of the plurality of segments. The converting can utilize an effective field size calculator or a ray tracer algorithm.

The comparing can also include displaying, at an electronic display, a report comprising the difference or generating, at an electronic device, a warning based on the difference.

The converting can also include accessing, from at least one database, a measurement of an output of the treatment beam, the patient image data, and a physical configuration of the radiation therapy system. Also, a conversion factor can be generated based on the accessed measurement, the patient image data, and the physical configuration corresponding to a segment. The conversion factor can be applied to the measured segment responses to generate the measured segment doses. A neural network can generate the predicted integrated image by weighting a predicted segment response contribution as part of an input layer of the neural network.

The patient image data comprises three-dimensional images of patient anatomy. Each of the segments can correspond to a time window where the delivery of dose to a portion of a patient anatomy is substantially constant. The segments can include at least one segment corresponding to less than 1 second of a treatment plan.

The comparison of measured segment doses to the desired doses comprises the comparison of a first sum of the measured segment doses to a second sum of the desired doses.

An electronic warning can be generated at a display device when the comparison of a first sum of measured segment doses to a second sum of the desired doses is outside of a predetermined dose limit.

Determination of the measured segment responses can also include extracting a predicted response contribution based on the predicted segment image data and the predicted integrated image. The measured segment response can be generated from the predicted response contribution and the transit data.

In an interrelated aspect, a method generates, at a server, a composite calibration image by operations including applying a first weight to a first calibration image from an electronic portal imaging device to generate a weighted first calibration image. A second weight is applied to a second calibration image from the electronic portal imaging device to generate a weighted second calibration image. The weighted first calibration image and the weighted second calibration image are superimposed to generate the composite calibration image. A dose calculation engine generates a composite dose map based on a first dose map, a second dose map, the first weight, and the second weight. At the server, a conversion factor is generated that converts images to dose maps, where the conversion factor corresponds to a first radiation therapy system configuration that is different than a second radiation therapy system configuration corresponding to at least one of the first calibration image or the second calibration image. The conversion factor is stored in a multidimensional conversion structure. The conversion factor generated from the composite dose map and the composite calibration image is transmitted from the server to a requesting device.

In some variations, one or more of the following features can be added, in any combination.

The conversion factor in the multidimensional conversion structure can be based on the composite calibration image and the composite dose map. The conversion factor can be generated by the superposition of more than two calibration images and more than two dose maps.

The conversion factors in the multidimensional conversion structure can be based on a plurality of basis parameters comprising at least one of an effective field size, a radiological path length, an exit distance, a pixel position, and a primary signal ratio.

The method can also include populating the multidimensional conversion structure with additional conversion factors corresponding to a range of primary signal ratios. The first weight can be a primary radiation fraction, the second weight can be a secondary radiation fraction, and the primary signal ratio can be based on the primary radiation fraction and the secondary radiation fraction.

The composite dose map can be generated by operations including generating a first dose map based on the first calibration image and a first conversion factor in the multidimensional conversion structure. A second dose map can be generated based on the second calibration image and a second conversion factor in the multidimensional conversion structure. The first dose map, weighted by the first weight, and the second dose map, weighted by the second weight, can be superimposed to generate the composite dose map.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

To effectively treat some patients with radiation, it can be necessary to apply varying amounts of radiation to different portions of a patient's anatomy and at different angles and rates of radiation exposure. These treatments can occur over an extended period of time, minutes, hours, or even days with different treatment sessions. To determine if the proper amount of radiation was given to a patient, a radiation detector can be used that detects the radiation exiting a patient and creates an electronic signal or digital output proportional to the amount of radiation received. Because the treatment conditions can change from moment to moment, the detected radiation can be considered as a combination of smaller, approximately constant, applications of radiation. The measurements of the detected exit radiation into these treatment segments can be converted to a dose. The measured dose can be compared to the exit detector planned or expected dose in order to evaluate the accuracy of the delivered treatment. The comparison can be done on a segment by segment basis, or for an integrated dose measured by the radiation detector.

Among the benefits described herein, the current subject matter allows an efficient and accurate method of determining a delivered radiation dose to the exit detector from a single integrated image (or dose map) formed from a superposition of individual detections that were generated under spatially and/or temporally varying conditions. For example, some radiation detectors do not have a means of extracting measurements with fine time-resolution. For example, some radiation detectors provide only a single integrated measurement available after a procedure. Where such limitations are present, computing an accurate dose based on the blended measurements can be inaccurate or extremely difficult. The implementations described herein address this technical problem, among others.

Some implementations described herein relate to the radiation detector being an EPID device. In other implementations, the radiation detector can be any type of radiation detector that performs substantially the same functions as an EPID. For example, the radiation detector could be a device that directly uses diodes without a phosphor. In yet other implementations, the radiation detector can include an array of ionization chambers or an array of individual scintillating elements. It should be noted that the detector elements of the exit detector need not lie in the same plane. For example, provided that the locations of each detecting element are known, these locations can be accounted for in the disclosed method. Thus a detector comprised of multiple planes or even a loose collection of detecting elements randomly located behind the patient can be used.

Figure 1:
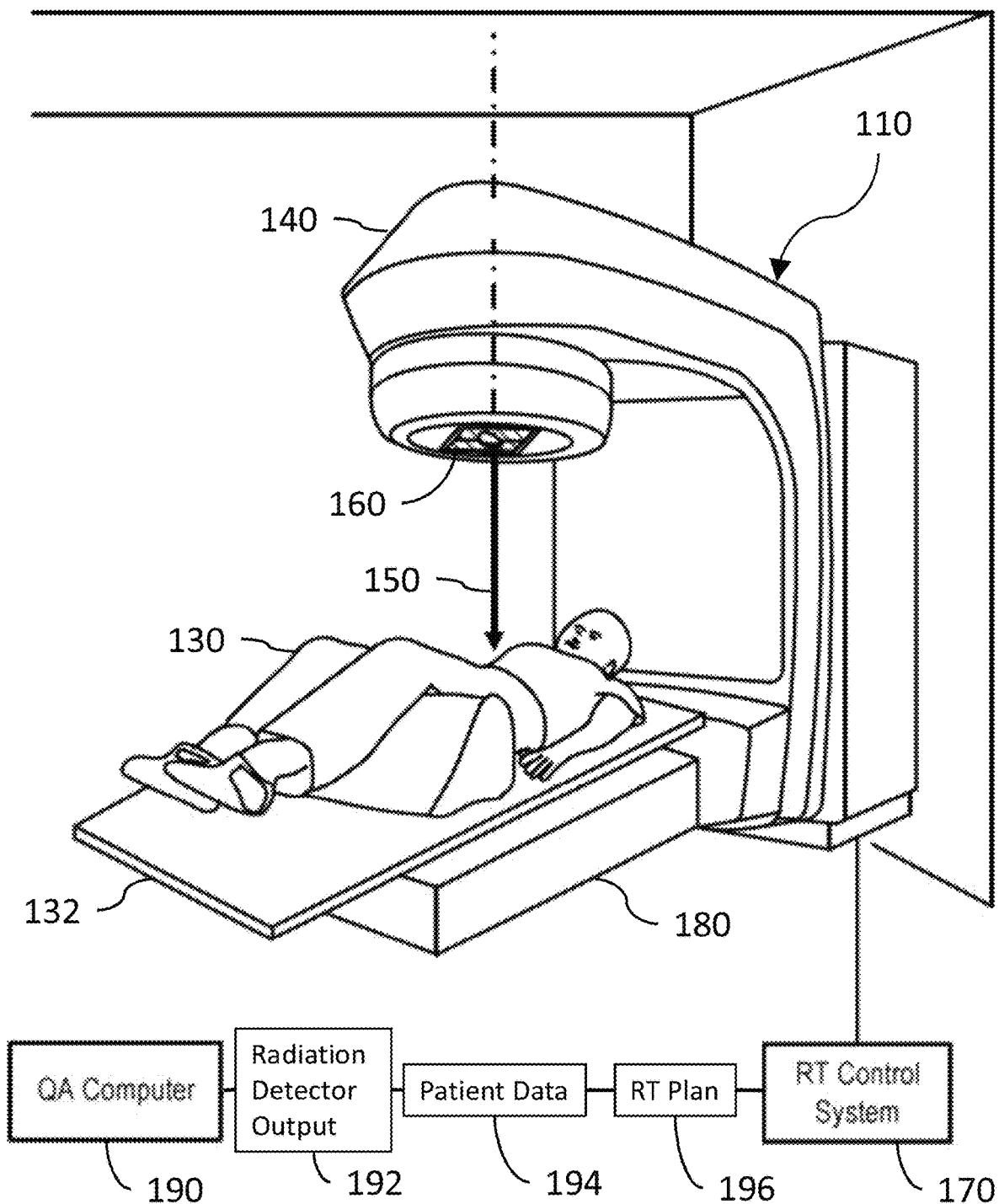
FIG. 1 is a simplified diagram illustrating a radiation therapy system equipped with a radiation detector for measuring radiation exiting from a patient in accordance with certain aspects of the present disclosure.

FIG. 1 is a simplified diagram illustrating a radiation therapy system 110 equipped with a radiation detector 180 for measuring radiation exiting from a patient 130 in accordance with certain aspects of the present disclosure. The radiation therapy system 110 can include a gantry 140 that can rotate about the patient 130. Inside gantry 140, there is a radiation source, for example, a linear accelerator (LINAC), cobalt 60 source, etc., that directs radiation toward patient 130 in the form of treatment beam 150. The treatment beam 150 can also include scanning beams, where a small beamlet is scanned over the area that is required to be treated. The treatment beam 150 may be shaped by a collimator 160, for example, a multi-leaf collimator (MLC), before reaching patient 130. In the example of the collimator 160 being a MLC, the collimation may block part of treatment beam 150 by providing a series of narrow gaps between opposite leaves of the MLC, which combine across multiple leaf pairs to form a desired shape, typically similar to the tumor that is being irradiated. The example of a multi-leaf collimator is used herein. However, the present disclosure contemplates any type of collimation device.

The treatment of patient 130 can be controlled by a radiation therapy control system 170, which can include, for example, processors, computers, hardware, computer programs, etc., that control the administration of a radiation treatment plan 196 for the patient 130. The radiation therapy control system 170 can control, for example, treatment beam 150, position of gantry 140, beam shape created by collimators 160, etc.

Radiation treatment plans, as used herein, can include any type of information about radiation delivery, such as a treatment plan, obtained in any manner, for example, delivery log information, or any measurements or other data that can provide information about the patient entrance fluence, etc. Typical radiation treatment plans further involve defining specific machine parameters at precise, and typically fine, time intervals to most closely deliver the specified dose of radiation to the target volume in the patient 130. Common parameters used in radiation treatment plans can include, for example, treatment beam shape or energy, orientation of the gantry, collimator leaf positions, patient anatomy (CT) image orientation with respect to the treatment beam, etc.

The patient 130 can rest on patient couch 132 during treatment. After radiation passes through patient 130 and, at times, patient couch 132, the radiation can impact radiation detector 180. In some implementations, radiation detector 180 can be connected to gantry 140 or otherwise made to rotate with gantry 140 or the radiation detector 180 can be comprised of a multitude of stationary or moving detectors positioned around the patient in a cylindrical or any other shape.

Radiation impacting the radiation detector 180 may be detected as a pattern related to the transmission and absorption of the radiation by the patient anatomy and/or tumor(s). In one type of detector, the radiation detector 180 may convert the incident radiation to other wavelengths of light, via a phosphor layer in radiation detector 180. Light from the phosphor may then be detected by photosensors and converted into an electrical signal, essentially creating a pixel map for the radiation incident on radiation detector 180. The electrical signals from radiation detector 180 can be acquired by, for example, analog-to-digital convertors, digitizers, etc. to acquire, filter, analyze, store or otherwise process the acquired exit radiation measurement information.

As part of the monitoring and quality assurance of radiotherapy treatment, systems and diagnostics can be used to estimate the dose delivered to the patient 130 and compare it to the goals specified by the radiation treatment plan. Such systems or software can be integrated into the radiotherapy control system or may be part of a separate quality assurance (QA) computer 190 (as shown in FIG. 1). While the embodiment described herein utilizes a separate quality assurance computer, the present disclosure contemplates the concepts disclosed herein being implemented within the radiation therapy system's control system or any other related system. Though FIG. 1 shows the QA computer 190 and the radiation therapy control system 170 as separate components, the functionality described herein can be performed on an integrated system or distributed across any number or type of hardware or software components that enable the specified functions herein to be performed.

Figure 2:
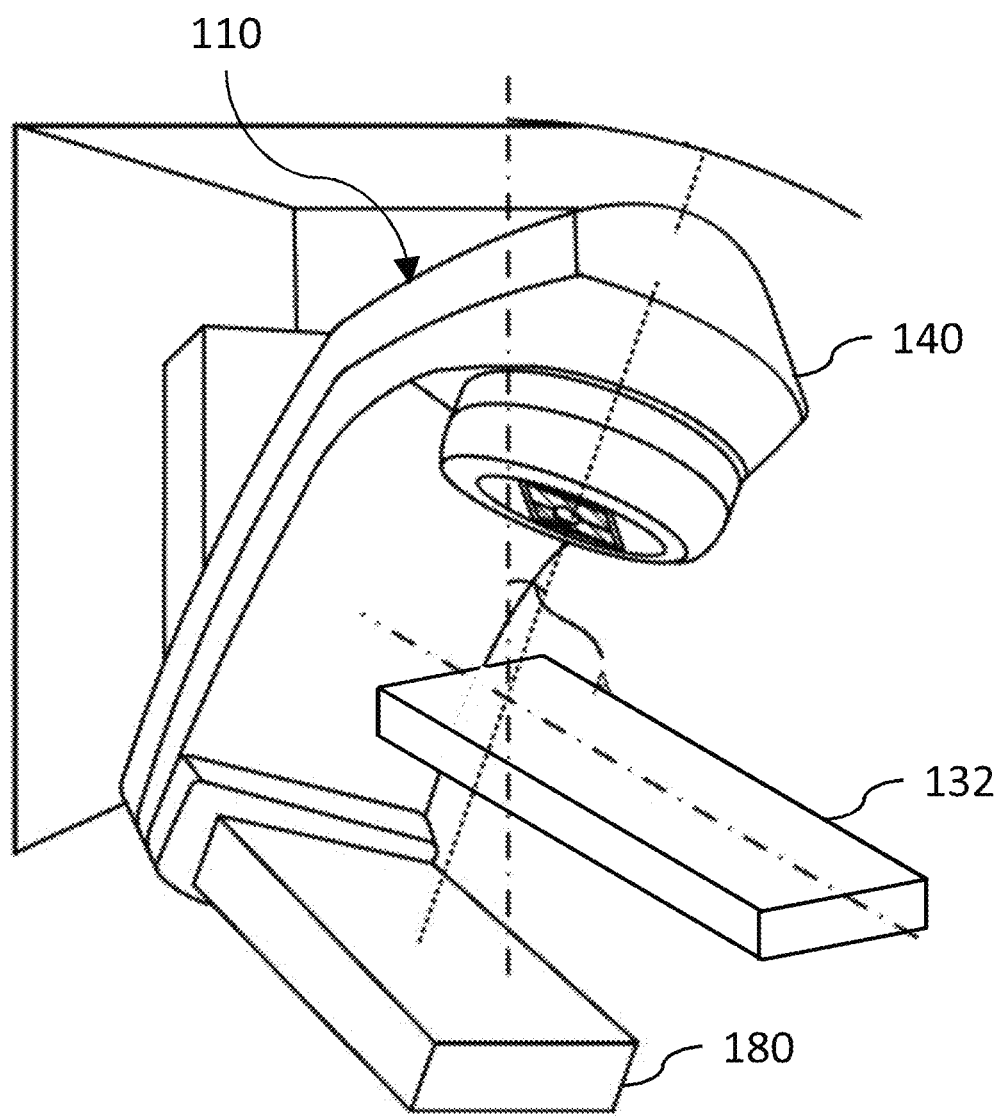
FIG. 2 is a simplified diagram illustrating the radiation therapy system rotated during patient treatment in accordance with certain aspects of the present disclosure.

FIG. 2 is a simplified diagram illustrating the radiation therapy system rotated during patient treatment in accordance with certain aspects of the present disclosure. The gantry 140 can rotate any number or portions of transits about the patient and or patient couch 132 such that the treatment beam 150 arrives at the patient at different angles while the distance from the point of beam emission to the radiation detector 180 can be constant. Due to the rotation of the gantry 140, the path of the treatment beam 150 through the patient can change. The treatment plan can control the angle of the gantry 140 (shown as angle A in FIG. 2), the apertures formed by any collimators, beam energy parameters, or the like.

During patient treatment, due to rotation of the gantry 140, the treatment beam 150 interacts with different parts of the patient anatomy. This, combined with the corresponding changes to treatment beam 150 output can create a varying intensity of radiation that is detected by the radiation detector 180. Over the treatment process, the accumulated signal due to each portion of the treatment plan can be considered as an integrated image (or transit image). As used herein, the term "transit image" can refer to any number or combination of individual images and/or measurements resulting from the detection of radiation at the radiation detector 180 during execution of the treatment plan. Additional details of the transit image are described below in the discussion of FIG. 3.

As described herein, in some implementations, verification of the dose received by the patient can be performed by comparing a predicted exit dose (based on the treatment plan) to a measured exit dose (based on the transit image received from the radiation detector 180). This comparison can be performed at each pixel of the radiation detector 180 and for individual segments of a patient treatment procedure. Further details of the verification process are described below.

Treatment plan information can be acquired from a radiation therapy system. Treatment plan information can include, for example, positions and/or angles of the gantry 140, energy of the treatment beam 150, collimator positions (including leaf positions in a multileaf collimator), treatment beam 150 on/off status, predicted target dose information at varying portions of the patient anatomy, acceptable limits or error in received patient dose, or the like. The treatment plan information can be acquired from a connected treatment computer or can be loaded onto the radiation treatment control system.

Patient image data can be acquired by an imaging system and can include images of the patient anatomy, for example, tissue, bone, tumors, cavities, or the like. Imaging devices that can generate the patient image data can include, for example, computed tomography systems, magnetic resonance imaging systems, x-ray systems, or any combination thereof. The patient image data can be in the form of static images or video images. The patient image data can be two-dimensional (as in single static image), two-dimensional plus time (as in a time sequence of two-dimensional images), three-dimensional (as in a number of static images acquired at different locations or planes in a three-dimensional space), or four-dimensional (as in a series of three-dimensional images taken at different times). Patient image data can include information about the physical location of the images, for example, coordinates, angles, or other identifying information specifying an image plane or location of an image volume. Similarly, when the patient image data has a temporal component, the patient image data can include timestamps or sequencing information that identifies either an absolute time between images or a relative or ordering of the images. In some implementations, the patient image data can be acquired prior to patient treatment and loaded into any of the systems described herein. In other implementations, the patient image data can be acquired later and the features relying on the patient image data can be performed post-treatment.

Figure 3:
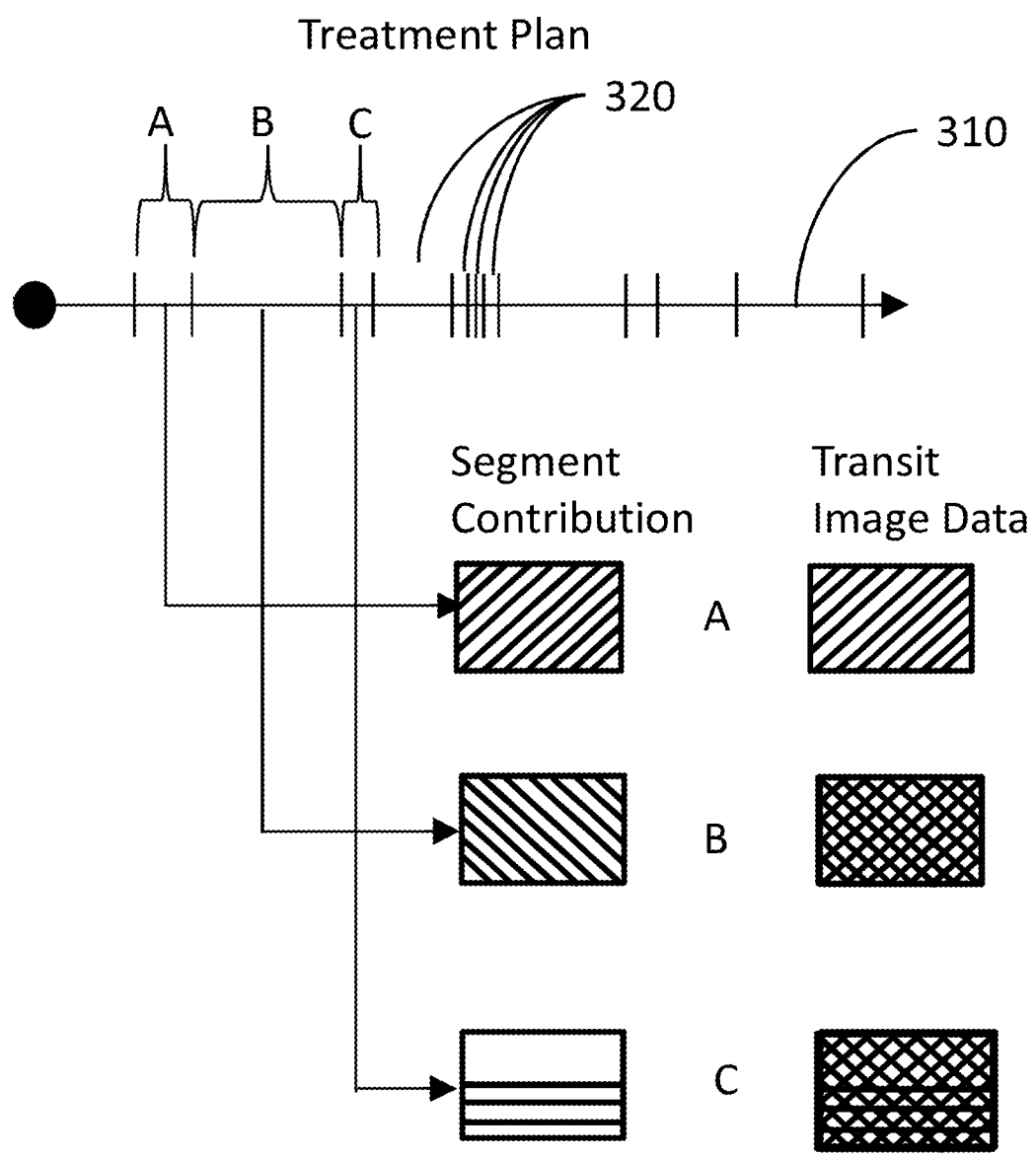
FIG. 3 is a simplified diagram illustrating formation of a transit image from execution of segments in a treatment plan in accordance with certain aspects of the present disclosure.

FIG. 3 is a simplified diagram illustrating formation of a transit image from execution of segments in a treatment plan in accordance with certain aspects of the present disclosure. Transit image data can be generated by a superposition of data received from the radiation detector 180 during radiation therapy. The timeline 310 shows an example of a treatment plan that proceeds by providing movement of the gantry 140, modification of collimator positions, variations in beam energy, etc. The treatment plan can be divided into segments 320, of varying (or constant) length. Each segment of the treatment plan contributes to the transit image that is ultimately generated from measurements at the radiation detector 180. Conceptually, this is illustrated in FIG. 3 by the two columns of images. In the example of FIG. 3, each row of images corresponds to different times during the treatment plan. The left column (segment contribution) represents the image contribution generated at the radiation detector 180 during segments A, B, and C. The right column (transit image data) represents the cumulative or integrated image at the radiation detector 180 after each of segments A, B, and C. The cumulative image corresponds to the transit image data, which is acquired over some or all of the patient treatment.

As a specific example, an EPID can measure an induced charge at a "pixel" (or other small detection area) of the EPID. The charge can be proportional to the amount of incident radiation at that pixel. The rate at which charge is acquired can vary with the application of the treatment plan and the location of the patient anatomy relative to the treatment beam 150. In this way, the transit image data can be the total charge stored on, or measured from, the radiation detector 180 over some or all of the treatment by the treatment beam 150. The transit image data (e.g. in terms of acquired charge) can be converted to another unit, such as a calibrated unit. The calibrated unit can represent the raw signal from the radiation detector 180 combined with a calibration factor to convert the physical quantity (e.g. charge) detected at a point or pixel on the radiation detector 180 to an image (e.g. an intensity, color, or the like).

In some implementations, the transit image data can be in the form of raw data (e.g. charge at the radiation detector 180) that has been post-processed and/or otherwise converted into viewable images. Transit image data of this type can be in the form of video or cine images spanning the treatment segments. Any number of frames of video can be combined into segments, and correspondingly any number of segments of video can be combined to form the transit image data.

Though the explanation of the transit image data provided above was described in terms of a superposition of images, the process can begin with the acquisition of the transit image data (e.g. an integrated image), with the separation into segments performed subsequent to patient treatment. Once all of the required data is acquired, the process of comparing the measured dose (e.g. determined from the transit image data as described below) to a desired dose (e.g. based on the treatment plan) can begin. As shown in FIG. 3, the treatment plan can be made up of a number of individual treatment steps where treatment beam 150 settings, patient position, gantry 140 angle, or the like, are substantially constant. In this way, each of the segments can correspond to a time window where the delivery of dose to a portion of a patient anatomy is substantially constant (e.g. not changing or changing only to a small and acceptable amount). In some implementations, a segment can be, for example, more than 1 second, 1 second, 0.5 seconds, 0.1 seconds, 0.05 seconds, 0.01 seconds, less than 1 second, less than 0.5 seconds, less than 0.1 seconds, or the like. In other implementations, the segments that make up a patient treatment need not be uniform in time. For example, during patient treatment, if the treatment beam 150 is on and the gantry 140 is in one particular spot for some relatively long span of time, this can correspond to a first segment spanning that long span of time. Then, if the gantry 140 rotates to another position and the treatment beam 150 is on for a short period of time, this can correspond to a second segment spanning that shorter length of time. In this way, the segments can vary in duration to capture a sequence of periods of substantially constant patient treatment. By dividing the treatment plan information according to these segments, each segment of the treatment plan information can also correspond to a constant flux of radiation to the radiation detector 180. Subsequently, the measured response (e.g. acquired charge) at the radiation detector 180 can be approximately linear in time over the span of the segment.

A prediction of what should be measured at the radiation detector 180 during a segment can be made. Predicted segment image data can be determined utilizing a predicted image calculation algorithm and at least the patient image data and the treatment plan information. The predicted segment image data can be, for example, a portion (corresponding to a segment) of the transit image that would result from the radiation treatment plan when the radiation treatment plan is administered as expected.

Under these conditions, knowing information about the state of the treatment beam 150, the position of the gantry 140, the anatomy of the patient (from the patient image data), and a calibration of the radiation therapy system 110 and the radiation detector 180, a predicted signal or measurement at the radiation detector 180 can be determined. For example, the output of the radiation therapy system 110 can be expressed in a radiation flux. The absorption or scattering of radiation by the patient anatomy, patient couch 132, and any other intervening materials, can be estimated based on measurements received at the radiation detector 180 during a calibration. Knowing the output of the radiation therapy system 110 specified in the treatment plan, this can be converted with the calibration to calculate the predicted segment image data. This can also involve taking into account the time duration of the particular segment. In this way, the predicted segment image data can be the product of the radiation flux reaching the radiation detector 180 and the calibration, summed over the duration of the segment.

Because some radiation detectors, EPIDs for example, have a large number of small detector surfaces (previously referred to as "pixels,") the measurements and predictions described herein can be performed on a pixel-by-pixel basis. Among other reasons, this is due to the fact that the treatment beam 150 (and the patient anatomy) may not be uniform when projected onto the surface of the radiation detector 180. Accordingly, many of the implementations described herein require their own calibration of the radiation detector 180 at each pixel and knowledge of the intervening patient anatomy and the angle and energy of the treatment beam 150 corresponding to that particular pixel.

In other implementations, the predicted segment image data can be generated by through use of a machine-learning program in which the element-by-element dose response is derived from a collection of prior patient or phantom measurements for which the treatment-time anatomy and thus detector dose was well-known. In other implementations, this machine-learning approach can be combined with the above-described approach using the measured calibration data by informing the implementation in which only measured calibration data is used.

In other implementations, a predicted segment image data can be generated by converting a predicted dose (for example from a radiation treatment plan, via Monte-Carlo simulation or any other computational algorithm capable of simulating the radiation behaviors of the detector's constituent components). The predicted dose can then result in a predicted signal contribution generated at the radiation detector 180 for a given segment directly or using the appropriate calibration factors for each segment.

In yet another implementation, direct Monte-Carlo simulation using the treatment plan and patient image data can be used to directly simulate the response of the detector to the patient exit radiation in order to calculate segment predicted images.

In yet another implementation, a measurement of the radiation fluence from detectors other than the EPID (e.g. near the radiation source, positioned at or around the radiation therapy system 110, etc.), or a calculation of the radiation fluence received by EPID pixels, can be converted into the predicted segment image data. For example, a signal from a radiation detector near the radiation source can be combined with the known collimator configuration, and patient image data (describing locations, orientations, and materials of the patient anatomy interacting with the treatment beam 150), to generate the predicted segment image data without reliance on measurement from the EPID.

In a further implementation, the predicted segment image data can be generated prior or after the generation of the transit image data. For example, predicted segment image data can be recalled from a database where the conversion of the transit data to dose has been performed. When the recalled predicted segment image data represents a successful operation of the treatment plan, the predicted segment image data can be used to assemble the predicted integrated image, without having to re-compute the predicted integrated image from the radiation treatment plan as described below. In another implementation, it is also possible to use measured segment-by-segment images of the patient, measured during another treatment session, as the predicted segment-by-segment image. Digitally reconstructed radiographs, or measured radiographs of the patient, can also be used instead of the predicted image.

A predicted integrated image can be determined through superposition of data and/or images from the predicted segment image data. In some implementations, the predicted integrated image can be the transit image that would be result from the treatment plan going as expected. To generate the predicted integrated image, one or more segments of the predicted segment image data can be combined. The combination can be, for example, of a scalar output of the radiation detector 180 (e.g. a measured current).

In other implementations, the predicted integrated image can be a digital superposition of a sequence of images generated from the predicted segment image data (e.g. when the predicted segment image data has been converted to a map or other visual image corresponding to a snapshot of the expected measurement at the radiation detector 180). In yet other implementations, the predicted integrated image can be replaced by a calculated cumulative dose to the radiation detector by the radiation exiting the patient. Here, the calculated cumulative dose to the radiation detector 180 can be converted to an integrated predicted image based on a known conversion factor, Monte Carlo simulations, prior patient data (e.g. known received doses from previous treatments under the same conditions), or the like.

As described above, the predicted segment image data can be determined on a pixel-by-pixel basis. Therefore, the predicted integrated image corresponding to the surface of the radiation detector 180 can be generated by summing the contributions, for each pixel, over all the segments. The pixels can then be arranged into the predicted integrated image based on the locations of the pixels on the radiation detector 180.

Measured segment responses can be determined from the transit image data utilizing the predicted segment image data and the predicted integrated image. The output (e.g. current, intensity, etc.) of the radiation detector 180 during a segment is the measured segment response. The measured segment response is similar to the predicted segment response, but refers to an actual measurement and not to an a priori calculated value as with the predicted segment response. In other words, the transit image data can be separated into measured segment responses according to the various contributions estimated from the predicted segment image data.

Because the predicted integrated image can be assembled from the superposition of the predicted segment image data, the fractional portion or ratio of the contribution of a predicted segment image data to the predicted integrated image can be estimated for each segment. The contribution can be referred to as the predicted segment response contribution.

For example, based on the treatment plan, it could be determined that the predicted segment response contribution for a specific area or pixel of the exit detector of a first segment was 1% of an expected transit image and the predicted segment response contribution of a second segment was 3% of the expected transit image. The predicted segment response contribution can then be multiplied by the transit image data to generate the measured segment response. This segmentation of the transit image data can provide benefits in dose verification since conversion to dose utilizes calibration factors that are dependent upon the state of the treatment delivery for each segment. The effective field size and distance the patient is from the exit detector are two examples of parameters that can describe the state of treatment delivery.

The measured segment responses can be converted to measured segment doses (the dose that the patient or detector received during a segment). This can be done by, for example, accessing, from a database, conversion factors based on the patient image data and a physical configuration of the radiation therapy system 110. The conversion factors can be generated based on a calibration procedure such as described in the subsequent section, in which the conversion factors depend upon, for example, the impact of the patient image data (or patient anatomy) on the radiation beam, the physical configuration (of the radiation therapy system) of the corresponding segment, and how close the patient is to the exit detector. The conversion factor can be applied to the measured segment responses to generate the measured segment doses. Also, the measured segment doses can be directly compared to calculated expected segment doses, if available, in order to provide additional verification.

In another implementation, the conversion factors can be modeled by analytical functions, and the analytical functions fitted to these calibration factors can be used instead of the conversion factors from the calibration table.

In yet another implementation, an artificial neural network can be trained that receives the aforementioned inputs used to determine the conversion factor, and provides the conversion factors from a calibration table as the output. Any other computational fitting algorithm could also be used in the same fashion.

The conversion factor can be a combination of one or more conversion factors that are based on machine status, image data, patient data, or the like. For example, based on the treatment plan and/or treatment logs, the input fluence, exit fluence, field size, beam energy, spectrum, and the like can be determined for each delivery segment and a calibration factor can be determined that converts a measured segment response of the transit image to a measured segment dose.

The treatment plan and/or treatment logs can be acquired or accessed from a treatment planning system or other connected computer. The treatment plan can describe portions of the patient anatomy and specify a target dose, acceptable dose ranges, times of treatment, radiation therapy system machine settings, a sequence of settings to be implemented during treatment, or the like. The treatment logs can include similar information as the treatment plan, with one difference being that the values contained in the treatment logs can be the actual values that the radiation therapy system 110 implemented during the actual delivery or the like.

The input fluence, the amount of radiation exiting the collimation systems prior to reaching the patient, can be determined from the treatment plan, treatment log files, or radiation measuring device near the treatment beam 150 source or disposed in the treatment area. The input fluence can be determined by converting a signal generated by the arrival of radiation at the diagnostic to the input fluence based on the calibration applied to the signal.

The exit fluence can include the energy spectrum or shape of the radiation pattern and direction of travel of the radiation waves received at the radiation detector 180. Attenuation and/or scattering from the patient and any other intervening physical structures can reduce the radiation reaching the radiation detector 180. The exit fluence can be considered as the input fluence minus the attenuation/scattering. Because of scattering or other distortions, the exit fluence pattern at the radiation detector 150 may not be the same as the radiation pattern that would occur in the absence of intervening material.

The field size can be based on a combination of collimator settings (either or both of multileaf collimators or collimating jaws), modeled estimates of the treatment beam 150 shape, or radiation scattered or leaked through the collimators during patient treatment. The beam energy spectrum can be determined based on radiation therapy system settings, measured or analytical spectra of the beam energy at given settings and mean beam energies, or the like.

The conversion factor can be a combination of a first conversion factor, a second conversion factor, and so on. In some implementations, the first conversion factor can include a number of independent basis parameters with a known relationship to a received dose. For example, a first conversion factor can include a factor based on field size, a factor based on radiological path length, an output factor (e.g. a dimensionless parameter describing a change in the output of the radiation therapy system 110 versus a change in the field size), electron density of the patient in between the source and the EPID, the patient exit distance to the detector, input fluence, exit fluence, or the like. Again, these factors can be independent from each other. In contrast, there can be a second conversion factor that is an amalgam that accounts for all remaining aspects of the system when converting a measured image to a measured dose. The second conversion factor can include a numerical scaling, factors based on the treatment plan and/or treatment logs, patient image data, or the like. Any of the conversion factors can be in terms of other parameters such as attenuation, electron density, equivalent water density, fluence received at the radiation detector 180, or the like.

In some implementations, the conversion factor can be based on data received from an effective field size calculator, a ray tracer algorithm, or an exit fluence calculation algorithm. The effective field size calculator can be, for example, the output of a Monte Carlo algorithm or other simulation module that takes into account beam parameters as well as any intervening collimation. The effective field size calculator also can be replaced by an output factor calculator which uses the same input parameters and provides a different output parameter that is in close relation with the effective field size/effective field width. The ray tracer algorithm can also utilize a model of a radiation source that provides an estimate of the trajectories of beamlets emitted from the source, to the patient, and to the radiation detector 180 as well as patient anatomical images or anatomical structure outlines with density overrides. The ray tracer algorithm can include modeling of a linear accelerator, or a point source, or a finite sized radiation source. The exit fluence calculation algorithm can process any combination of information from the patient anatomy data, radiation detector measurements, and the treatment plan to generate data or images representing the exit fluence.

Any of the conversion factors can be accessed from a computer memory or a database where the conversion factors are stored. The conversion factors can be in the form of a table, array, or representation of an analytical expression defining the conversion factor (e.g. equation coefficients). Similarly, any of the image data, radiation detector measurements, segment data, or the like, can be stored as tables, arrays, memory objects, image files, video, and the like. Any number of parameters can be combined from any number of conversion factors to convert the measured segment response to a measured segment dose. For example, the measured segment response can be a dimensionless number or some other unit. Upon applying the conversion factor, the measured segment response can be in terms of, for example, Gy or rads.

In some implementations, the conversion factor can be determined by implementation of a Monte Carlo method that takes into account variations in scattering and absorption of radiation by materials present along the radiation path. The materials can be determined from the radiation therapy system 110 setup (e.g. patient couch 132 dimensions, air scattering) and also from the patient image data.

In other implementations, an inverse process can be performed where predicted transit image data can be generated. Here, beginning with a predicted segment dose or a predicted integrated dose, these quantities can be multiplied by the inverse of the corresponding conversion factors. This can generate predicted segment image data or predicted transit image data, respectively.

In another implementation, the measured segment responses along with the corresponding conversion factor of each segment can be used as inputs to a machine-learning program or neural network that generates the measured segment dose. For example, a large variety of samples of the weighting given to different measured segment responses along with the corresponding conversion factor of each segment and the corresponding segment dose that provides the simple output results can be provided in the training stage of the neural network. The training set could be generated from a database of multiple patients, phantoms, or of the same patient getting the treatment. Once the training is successfully performed, the artificial neural network can provide an optimized measured segment dose.

In another implementation, the predicted segment response contribution can be determined with a machine-learning program or neural network as well. Such artificial neural networks can receive the relevant per segment parameters that affect the conversion factor of each segment as the input. The output of such a neural network can be the segment response contribution in percent or any other unit. The sample training data for such a neural network could also be provided from a single or multiple patient's treatment. The sample training data for a neural network can also come from plans specifically designed for such training, or from a calibration process on phantoms. In any of the neural network processes described herein, the weights can be applied at an input layer or hidden layer when generating the desired output.

In another implementation it is also possible to combine two artificial neural networks from above in a fashion that the outputs from the latter (e.g. based on training/calibration plans) becomes the input to the former (e.g. based on patient treatment data). Therefore, it is possible to make the first artificial neural network mentioned above a hidden layer in the combined artificial neural network. In another implementation, the inputs to both of the neural networks above, except for the segment weights, can be the input to a larger artificial neural network that can provide the final cumulative dose as the output using the same training datasets mentioned above. In one implementation, the artificial neural network can perform this process for all pixels at once. In another implementation, different artificial neural networks could be trained for different pixels or different groups of pixels.

A measured dose map that includes a sum of the measured segment doses in the radiation detector 150 can be compared to a planned dose map for the radiation detector 150 to assess radiation treatment delivery. The planned dose map can be based on the treatment plan information. Before patient treatment, the planned dose at a given point in the patient anatomy is determined during the planning process. This determination can drive optimization of the treatment plan and set the parameters used by the radiation treatment device. After the measured segment dose is determined, the measured dose map (or individual measured segment doses) can be compared to planned dose map specifying a desired sum of doses (e.g. generated from the treatment plan) to determine if the treatment went as planned. In some implementations, when a difference is detected between the measured dose map and the planned dose map, at one or more pixels in the radiation detector 180, a warning, report, or the like can be provided. The providing can be in the form of generating and displaying a report including a comparison of a measured dose map to a planned dose map. In other implementations, the providing can be in the form of generating a warning based on the difference of the measured dose map to the planned dose map. The warning can be further based on the measured dose being outside of a predetermined dose limit. The warning can be text or images generated and displayed at a computing device.

In other implementations, if one or more points in the dose difference map exceed a preset user-defined tolerance, the radiation therapy system 110 can be interrupted during delivery of radiation. This interruption can include transmitting a command to a control system to cause, for example, cessation of emission from the radiation beam source, closing of a collimator (e.g. jaws or an MLC), or the like, to guard against potential misadministration and allow clinical personnel adequate time to determine why the specified tolerance was exceeded.

Figure 4:
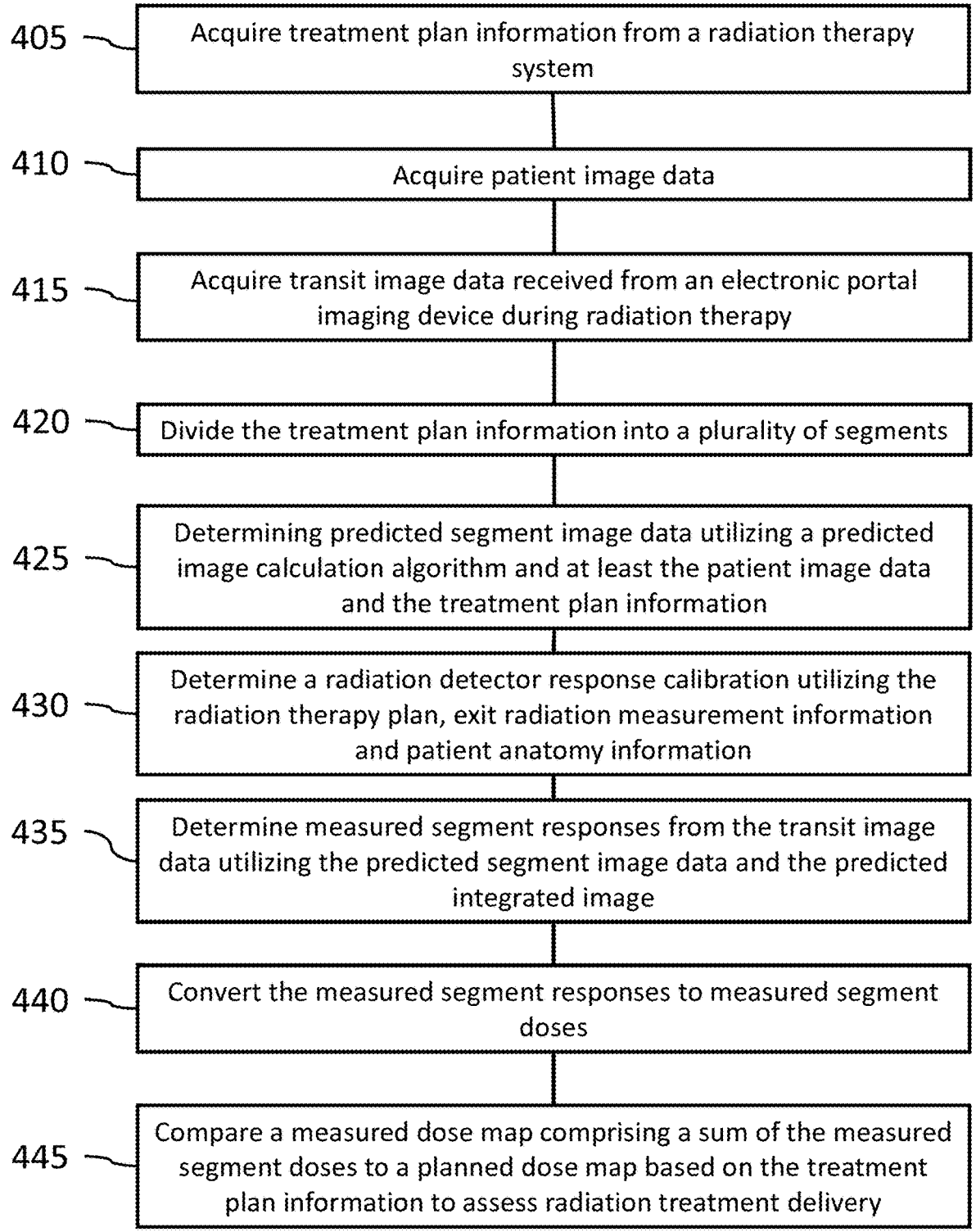
FIG. 4 is a process flow diagram illustrating a method of verifying a delivered radiation dose in accordance with certain aspects of the present disclosure.

FIG. 4 is a process flow diagram illustrating a method of verifying a delivered radiation dose in accordance with certain aspects of the present disclosure.

At 405, treatment plan information can be acquired from a radiation therapy system 110.

At 410, patient image data can be acquired.

At 415, transit image data received from an electronic portal imaging device during radiation therapy can be acquired.

At 420, treatment plan information can be divided into a number of segments.

At 425, predicted segment image data can be determined utilizing a predicted image calculation algorithm and at least the patient image data and the treatment plan information.

At 430, a radiation detector response calibration can be determined utilizing the radiation therapy plan, exit radiation measurement information, and patient anatomy information.

At 435, measured segment responses can be determined from the transit image data utilizing the predicted segment image data and the predicted integrated image.

At 440, the measured segment responses can be converted to measured segment doses.

At 445, a measured dose map comprising a sum of the measured segment doses can be compared to a planned dose map based on the treatment plan information to assess radiation treatment delivery.

Figure 5:
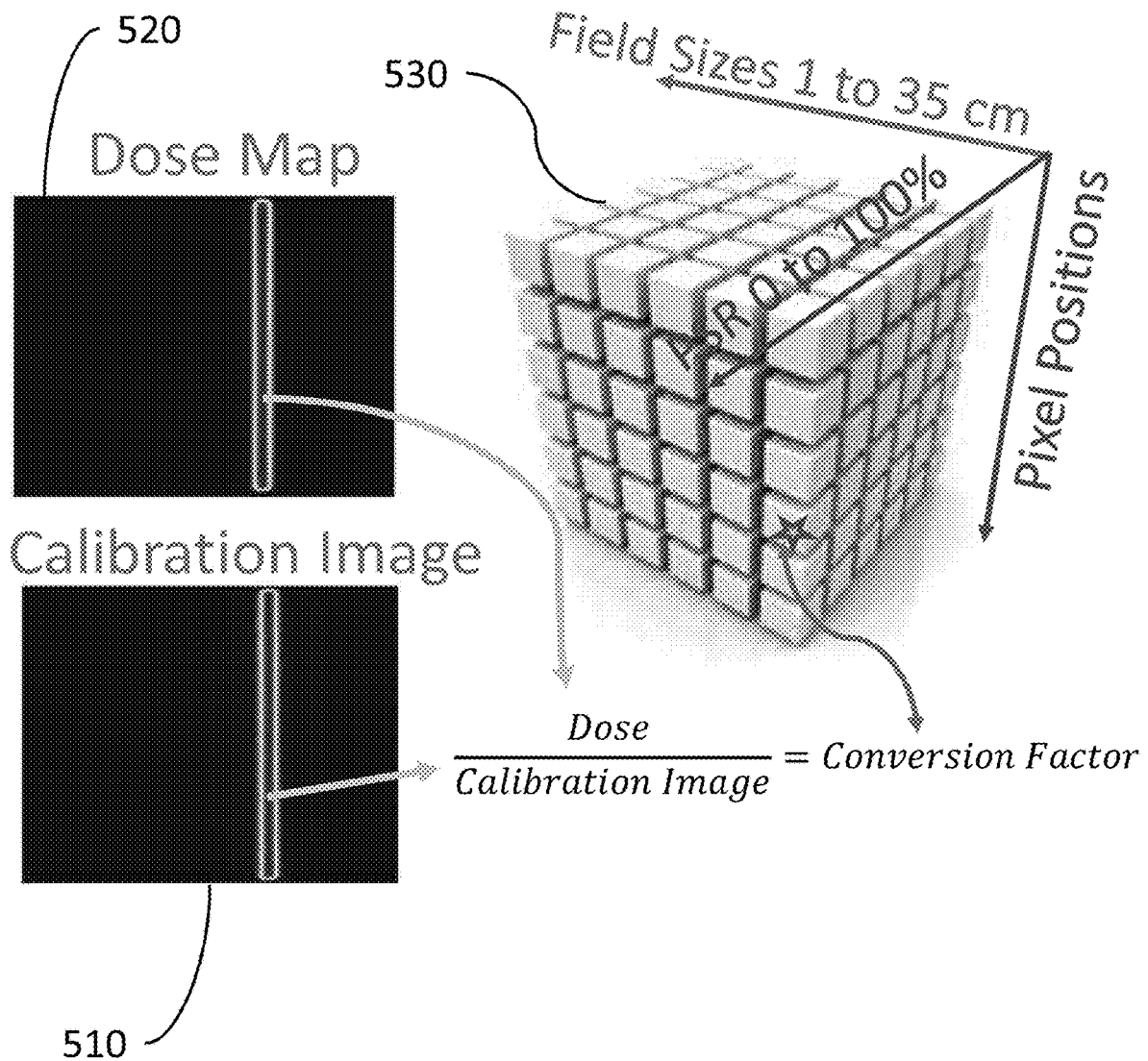
FIG. 5 is a simplified diagram illustrating conversion factors calculated from a calibration image and a dose map and stored in a multidimensional conversion structure in accordance with certain aspects of the present disclosure.

FIG. 5 is a simplified diagram illustrating conversion factors calculated from a calibration image 510 and a dose map 520 and stored in a multidimensional conversion structure 530 in accordance with certain aspects of the present disclosure.

Radiation detectors can be calibrated to provide a conversion factor between a measured response and an actual dose delivered to a patient or calibration object. In some cases, a limited set of conversion factors can be available based on a finite number of radiation therapy system configurations. In these cases, there can be a need to determine additional conversion factors for radiation therapy system configurations that were not used in a previous calibration. To provide the additional conversion factors, available calibration images can be weighted and combined to generate composite calibration images representative of the desired radiation therapy system configurations. Similarly, a dose calculation engine can provide an estimate of the dose delivered under the desired system settings. The estimated dose and the composite calibration images can be used to generate the desired conversion factors.

As described herein, the response of the radiation detector can be affected by a number of factors. These factors can include, for example, the pixel position on the radiation detector, an effective field size or output factor, whether the incoming radiation is primary (e.g. directly from the source and/or through a patient) or scattered (e.g. radiation scattered from the patient or other object that eventually reaches the radiation detector, patient exit distance to the radiation detector 180, radiological path length, and the like. A conversion factor can convert the response of the radiation detector (e.g. in the form of a calibration image) to a dose.

Each factor that affects the response of the radiation detector can act as a basis parameter for a conversion factor. The basis parameters in many cases can be independent, but it is contemplated that some basis parameters can be interrelated. Assuming independent basis parameters, a conversion factor can be expressed as $$C = f(x_1, x_2, x_3, \ldots). \quad (1)$$

Any number or combination of basis parameters can be used to determine the conversion factor. In one example, $x_1$ can be a pixel position, $x_2$ can be an effective field size, $x_3$ can be a primary signal ratio (PSR) (e.g. a fraction of time in the treatment plan when the pixel is in the direct path of the radiation beam 150), patient exit distance to the detector, radiological path length, patient exit fluence, or the like.

In one implementation, the response of the radiation detector 180 can be based on the primary signal ratio. Based on the system geometry and the radiation treatment plan, it can be determined whether a pixel of the radiation detector 180 is being exposed to primary radiation. For example, if a pixel (e.g. a center pixel) is in the radiation beam path during the entire treatment plan (e.g. not blocked by any collimation), then the primary signal ratio for that pixel would be 1.0. Similarly, a pixel that was exposed to the radiation beam 150 for 75% of the treatment plan would have a primary signal ratio of 0.75. It can be assumed, in this implementation, that the response of the radiation detector is directly proportional to the primary signal ratio.

In other implementations, the response of the radiation detector 180 can be based on a ratio of the actual amount of primary radiation reaching the radiation detector 180 to the actual amount of secondary radiation reaching the radiation detector 180. With the primary signal ratio, it can be assumed, in some implementations, that the signal is full strength when the pixel is in the direct path radiation beam 150 and zero when it is not. A more complicated representation can include determining the contribution of secondary radiation based on the treatment plan and the system geometry. For example, all pixels can be receiving some amount of secondary radiation due to scattering, beam edges, or the like. The total radiation at a pixel can then be the sum of the primary radiation can be the sum secondary radiation. Different dose calculation engines or Monte Carlo simulations can also be used for determining the primary and secondary radiation contribution to each pixel or groups of pixels.

Some radiation detectors, for example EPIDs, can have a different response to primary radiation (e.g. along the direct path of the radiation beam 150) than to secondary radiation (e.g. received at the pixel through scattering). For example, a given amount of primary radiation can generate a primary dose measured at the EPID. Similarly, the same amount of secondary radiation can generate a secondary dose at the EPID. Because of the difference in the EPID response between the two radiation types, the primary dose can be different than the secondary dose. In some implementations, the primary dose can be expressed as $$\alpha(\text{EPID response primary}) = \text{Primary Dose} \quad (2)$$

Similarly, the secondary dose can be expressed as $$\beta(\text{EPID response secondary}) = \text{Secondary Dose}. \quad (3)$$

In Eqs. 2 and 3, $\alpha$ and $\beta$ are EPID response coefficients for the different types of radiation.

In both implementations above, the measured dose at the radiation detector is linear with the measured response. Accordingly, a linear fit can be applied to the calculated dose versus response data. The slope of the linear fit can be stored as the conversion factor corresponding to a particular set of basis parameters (e.g. pixel position and field size). It should be noted that even though the relationship between the response and dose can seem like a linear correlation, the $\alpha$ and $\beta$ and can be very complex functions of other parameters that affect the calibration such as field size, radiological path length, beam energy, fluence mode, detector position, patient exit distance to the radiation detector 150, etc. In the simplified example presented in FIGS. 5 and 6, where the patient is not present, $\alpha$ and $\beta$ and are only dependent on the pixel position, PSR and field size. In more complex cases, when a patient or attenuator is present in the beam, there can be one such 3D matrix for each amount of attenuation and patient exit distance to detector. In such a case, it is also possible to store the exact same information in a 1.5 dimensional array. It is also possible to further refine these conversion factors by introducing more factors that could affect conversion factors. There can be more dimensions added to this multidimensional array of conversion factors as more conversion affecting parameters are taken into account.

A multidimensional conversion structure 530 can be generated to allow storage and access of the conversion factors $\alpha$ and $\beta$ and or any parameter that is a more complex function of both parameters along with any other aforementioned parameters such as PSR and field size, among others. The multidimensional conversion structure 530 can be a multidimensional array, a matrix, collection of tables, objects or code modules, or the like. As such, the multidimensional conversion structure 530, stored on a server or other computer device or computer memory, can be populated with conversion factors that relate a calibration image 510 to a dose map 520. The conversion factors can include a first conversion factor calculated, based on a first radiation therapy system configuration, to convert a first calibration image (e.g. characterizing the EPID response) from a radiation detector (e.g. the EPID) to a first dose map 520. A radiation therapy system configuration (and basis parameters) can include any combination of, for example, the pixel position, effective field size, PSR, beam energy, beam fluence mode, collimator settings, exit length, or the like.

In the example illustrated by FIG. 5, the multidimensional conversion structure 530 is shown conceptually as a cubic structure with each dimension corresponding to a basis parameter (e.g. effective field size, pixel position, and PSR). The conversion factor corresponding to a PSR of 1.0 (100% primary radiation) at a particular field size and pixel position is indicated by the star.

In some implementations, the calibration image 510 can be stored as a two dimensional image with each pixel or coordinate of the calibration image 510 having an associated intensity or value. The intensity or value of the calibration image 510 can represent the measured response of the radiation detector acquired during a calibration. Similarly, using a dose calculation engine, a dose map 520 can be generated with dose values that correspond to a predicted dose based on the settings present during the calibration. In the example illustrated by FIG. 5, the measured values of the calibration image are represented by different colors. Either on a pixel by pixel basis, or using entire images (e.g. 2-D, 3-D, etc.), the conversion factors can be determined by dividing the values comprising the dose map 520 by the values comprising the calibrated image. As used herein, the terms "map" and "image" can refer to a single element or value, a one-dimensional array or list of values, a two-dimensional array or table, up to an arbitrary dimensionality of the input data (e.g. dose values and/or calibration images).

Also, as illustrated in the example illustrated by FIG. 5, the pixel positions can be expressed in terms of ordered pairs (e.g. X and Y coordinates on a surface of the radiation detector). In this way, the pixel positions can be expressed as a basis parameter even though they refer to points on a two-dimensional surface.

The multidimensional conversion structure 530 can also include a second conversion factor converting, based on a second radiation therapy system configuration, a second calibration image from the radiation detector to a second dose map 520.

As mentioned above, there can be a request for a third parameter affecting the conversion factors, for example, the Primary Signal Ratio (PSR). The PSR is always 100% when comparing a single calibration response image and its corresponding predicted dose map. In the next section, we introduce a novel method that can use a limited number of individual calibration images for the purpose of finding the conversion factors, for example, for a set of PSRs (other than 100%), a set of radiological path lengths other than the ones measured, effective field sizes other than the ones measured, exit distances other than the ones measured, or other parameters that affect the conversion factors and have not been determined yet. The request can be made to the server from a requesting device, or from another program operating on the server.

Figure 6:
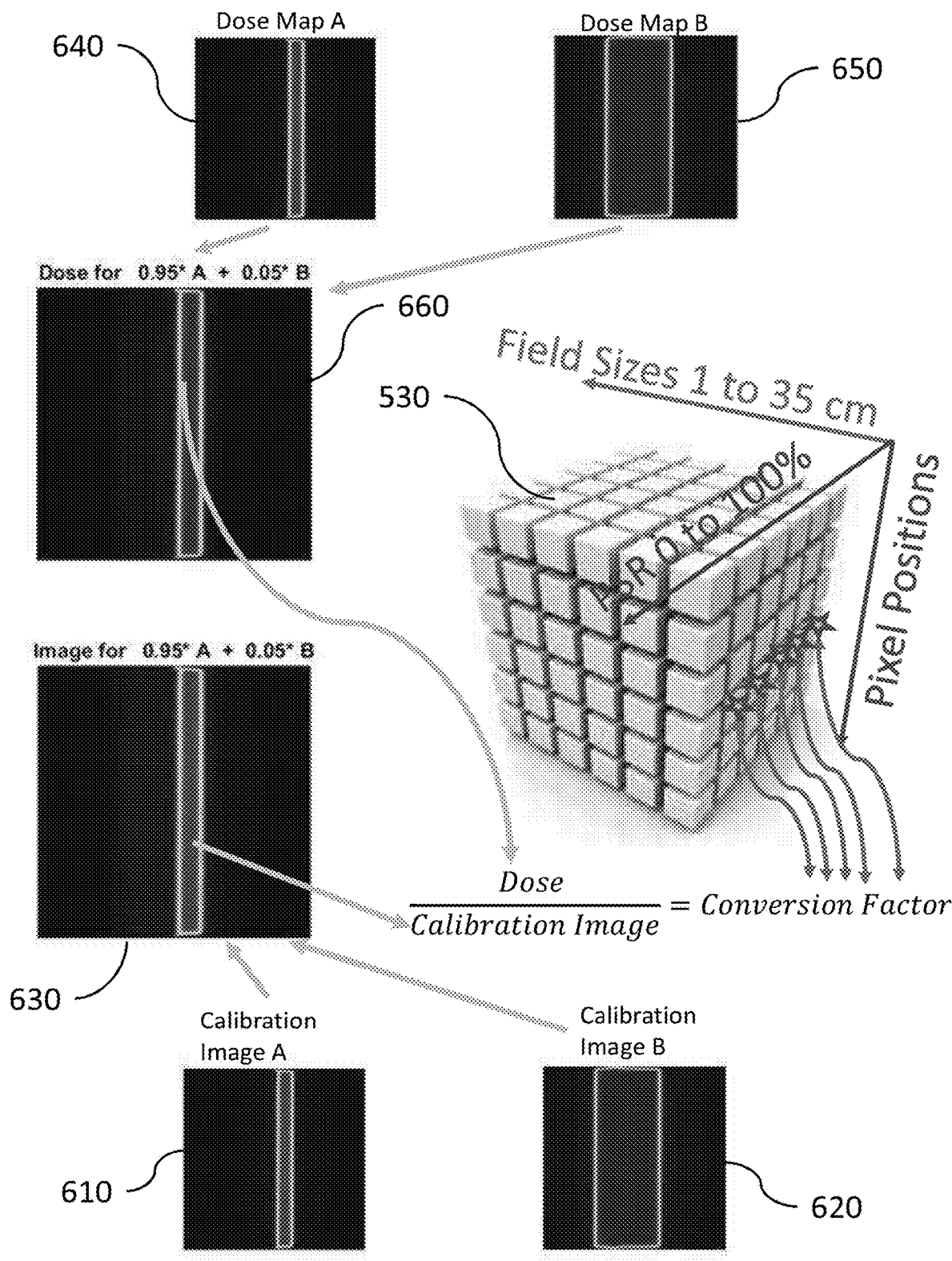
FIG. 6 is a simplified diagram illustrating superposition of images to generate additional conversion factors in the multidimensional conversion structure in accordance with certain aspects of the present disclosure.

FIG. 6 is a simplified diagram illustrating superposition of images to generate additional conversion factors in the multidimensional conversion structure 530 in accordance with certain aspects of the present disclosure.

As discussed above, is not always possible to perform a separate radiation delivery and a dose calculation in order to collect the correct measured calibration image and predicted dose map for determining every conversion factor in the multidimensional conversion structure 530. This is because the number of required measurements and dose calculations can be extremely large, due to the large dimensionality of the multidimensional conversion structure 530. In order to achieve the calculation of the conversion factors for additional (or every) cell in the multidimensional conversion structure 530, two or more dose maps can be combined with the corresponding calibration images with different weights in order to provide the desired conversion factor (e.g. another conversion factor). Use of different weights guarantees that we find conversion factors, for example, for all possible PSRs, radiological path lengths, exit distances to the radiation detector 180, effective field sizes, or output factors. For example, in FIG. 6, any point inside the vertical band in Image B that is not in the vertical band of Image A has a PSR of 5%, while all the pixels that are in the vertical band of A and B have a PSR of 100%.

In some implementations, a composite calibration image 630 can be generated at the server by performing the following the following operations. A first weight can be applied to the first calibration image 610, for example from an EPID, to generate a weighted first calibration image. A second weight can be applied to the second calibration image 620, which can also be from an EPID, to generate a weighted second calibration image. Then, the weighted first calibration image can be superimposed with the weighted second calibration image to generate the composite calibration image 630. Also, the dose calculation engine can generate a composite dose map based at least on a first dose map (such as the calculated expected dose for calibration image A), a second dose map (such as the calculated expected dose for calibration image B), the first weight, and the second weight. It is also possible to calculate the corresponding parameters such as the effective field size, radiological path length, and patient exit distance to EPID for this combination of the two calibration images and/or dose maps.

One example of this process is illustrated in FIG. 6. In this example, the request could be for a conversion factor corresponding to a PSR of 0.05. Here, this conversion factor does not presently exist in the multidimensional conversion structure 530. However, a first calibration image 610 (calibration image A) corresponding to a PSR of 1.0 can be combined with a second calibration image 620 (calibration image B) corresponding to a PSR of 1.0. To generate a composite calibration image 630 corresponding to a PSR of 0.05, the first calibration image 610 can be weighted (e.g. multiplied) by 0.95 (e.g. a primary radiation fraction) and the second calibration image 620 can be weighted by 0.05 (e.g. a secondary radiation fraction). The resultant composite calibration image 630 can be the sum or superposition of the two images. The effective field size of the superposition result, for example, can be calculated using a weighted average of the two field sizes combined to create the superimposed image.

The process outlined above can also include generating, by a dose calculation engine, a composite dose map 660 based on the first dose map 640, the second dose map 650, the first weight, and the second weight. The dose calculation engine can be, for example, a code module, separate computer, that can generate a dose based on input parameters including, for example, calibration data (e.g. calibration images), the treatment plan, or any combination thereof. Dose maps corresponding to the weightings can be also generated by inputting the unweighted calibration images (e.g. calibration image A and calibration image B) to the dose calculation engine.

In the example shown in FIG. 6, the dose calculation engine can generate a first conversion factor (converting the first calibration image 610 to a first dose map 640, e.g. dose map A) and a second conversion factor (converting the second calibration image 620 to a second dose map 650, e.g. dose map B). These dose maps can be weighted by the respective weightings that are applied to the calibration images. The composite dose map 660 can be generated by superimposing the first dose map 640, weighted by the first weight, and the second dose map 650, weighted by the second weight. Referring back to the example shown in FIG. 6, dose map A 640 can be weighted by 0.95 and dose map B 650 can be weighted by 0.05 into a composite dose map 660 with a PSR of 0.95.

In some implementations, the server can generate conversion factors that convert images to dose maps. The conversion factors can correspond to radiation therapy system configurations that were not present or used in generating the calibration images. In one example implementation, the conversion factor can correspond to a first radiation therapy system configuration that is different than a second radiation therapy system, such as one corresponding to at least one of the first calibration image 610 or the second calibration image 620.

Accordingly, in some implementations, the conversion factor can be generated that can convert the composite calibration image 630 into the composite dose map 660. For example, the conversion factor can result from the composite dose map 660 divided by the composite calibration image 630 which was generated using a different set of weights or different set of images, as shown by the equation in FIG. 6. The conversion factor can be stored in multidimensional conversion structure 530. The conversion factor, generated from composite dose map 660 and composite calibration image 630, can be transmitted from the server to the requesting device. As such, the implementations described herein provide a number of technical benefits, including allowing generation of additional conversion factors (shown as stars in FIG. 6) to be populated in the multidimensional conversion structure 530 that may correspond to radiation therapy system configurations not already represented in the multidimensional conversion structure 530. The additional conversion factors, in the example shown in FIG. 6, can correspond to a range of PSRs.

In other implementations, the conversion factor in multidimensional conversion structure 530 can be based on, for example composite calibration image 630 and composite dose map 660. In some implementations, the conversion factor can be generated by the superposition of more than two calibration images and more than two dose maps.

In some implementations, the server can be, for example, part of the radiation therapy system, a mainframe, a database, or the like. The requesting device can be an internal component of the server, such as another processor or requesting program. The requesting device can also be a client computer, for example, a computer used by quality assurance personnel or a clinical worker, or the like.

The examples given herein, in particular with reference to FIG. 5 and FIG. 6 generating composite images from different PSRs, are not limiting. The method of generating composite images (and their corresponding conversion factors) can be based on any of the basis parameters. For example, the above method can be used to generate a conversion factor corresponding to a missing effective field size measurement. Similarly, the method can be applied to generate a conversion factor corresponding to, for example, a pixel position, patient exit distance to the radiation detector 180, radiological path lengths, or other parameters missing in the multidimensional conversion structure 530. Other parameters can include, for example, leakage through a collimator (MLC or jaws), an average exit distance, a local exit distance, a product of the local exit distance and the radiological path length, or the like. The local exit distance can be the distance from the patient to the detector. Due to the shape and contours of a patient's body, this can be different than a constant distance such as the surface of a patient couch to a detector surface. The example given with the PSR is only one example and should not be considered as a limiting or exclusionary feature. In this way, any combination of the parameters can be used to generate the conversion factors.

Also, the conversion factors generated according to the above methods can be implemented when determining dose due to segment contributions of transit image data. For example, a segment of the treatment plan may not have a needed conversion factor for the dose contribution for the segment. The above method can be used to provide the needed predicted dose contribution. The predicted dose contribution can be converted to the corresponding predicted segment image data with the calibration factor. The predicted segment image data can be superimposed to generate the predicted integrated image, as described above.

In some implementations, the calibration process described above could be performed in a model development stage to populate the initial conversion factors and the conversion table could be adjusted for a user's treatment delivery machine based on a different method using a limited number of measurements.

Generating additional conversion factors can provide a more detailed multidimensional conversion structure 530, and hence a more robust calibration. Generating the dose maps and corresponding measured detector images to cover all possible calibration affecting parameters such as field size, PSR, radiological path length, patient exit distance to detector and can require a significant amount of dose calculation time as well as measurement time on the treatment delivery machine. To put it in perspective, if we only perform the calibration dose calculation and measurements for 10 field sizes, 10 different PSRs and 10 different radiological path lengths (10 different thickness of material, and 10 different patient exit distances for 10 different pixels, we would require to perform the dose calculations and measurements for 105 (10×10×10×10×10) different configurations that is extremely difficult to perform. However, using the methodology explained in this document, it is possible to perform a calibration with similar accuracy, only by performing as low as 50 (10+10+10+10+10) measurements. The numbers used here should not be limiting and it is clearly possible to further reduce the number of calibration measurements mentioned here. Another benefit can be the improved memory use and processing time of a computer tasked with providing conversion factors upon demand once the conversion factors are precalculated and the multidimensional array is repopulated. For example, the multidimensional conversion structure 530 can represent a sparse data set (i.e. one taking up less computer memory). However, with the above method, conversion factors can be generated or provided on demand without having to significantly expand the memory required for the multidimensional conversion structure 530. With a sparse multidimensional conversion structure 530, access time and file size can be reduced. As a result, desired calibration points can be generated in fewer processing cycles. Filling the multidimensional conversion structure 530 with all desired points would be an approximately $O(N^M)$ operation, where N is an average number of elements in a basis parameter and M is the dimensionality of the multidimensional conversion structure 530. This extremely expensive operation can be reduced to approximately $O(AN*M)$, where A is an average sparseness of the multidimensional conversion structure 530. Furthermore, because the desired conversion factor can be determined on demand (and not necessarily stored in the multidimensional conversion structure 530), any conversion factor can be determined while retaining an approximately constant memory allocation. As can be seen, the benefits of the procedures described herein provide greater benefits when the number of basis parameters is larger (i.e. when the conversion factor is more accurately represented). Also, any of the methods described herein can be implemented on a neural network or other artificial intelligence framework to optimize the generation of conversion factors that can be used in a dose verification process.

In one such implementation, an artificial neural network can be designed to receive the some or all of the calibration determining parameter as the input. The output, in one implementation, can be the conversion factor. The data generation process, using the superimposing procedure explained above, can be used to generate a large training dataset that provides the sample input parameters. The sample output parameter/parameters can be generated by dividing the composite calibration dose by the composite measured calibration image. In some implementation, a single artificial neural network with any arbitrary number of inputs or outputs can be created that receives the input parameters for a single pixel or a group of pixels and yields the conversion factors, as well as other arbitrary outputs of a single pixel or a group of pixels. These trained artificial neural networks can also be a hidden layer in a larger artificial neural network capable of providing the conversion factors for all pixels of the detector at once. In other implementations, a single artificial neural network can be trained for a constant condition or parameter. For example, a single parameter, such as field size, can be held constant. This single parameter can be provided as input to the single artificial neural network, as well as providing the rest of the parameters affecting the conversion factor. In this way, the single artificial neural network can receive the needed parameters, and either including or excluding the constant factor. In such implementation, a specific neural network trained for the corresponding conditions in each segment can be used for finding the conversion factor of that particular segment. Multiple neural networks could be linked for each segment in such an implementation to generate the final conversion factor.

Figure 7:
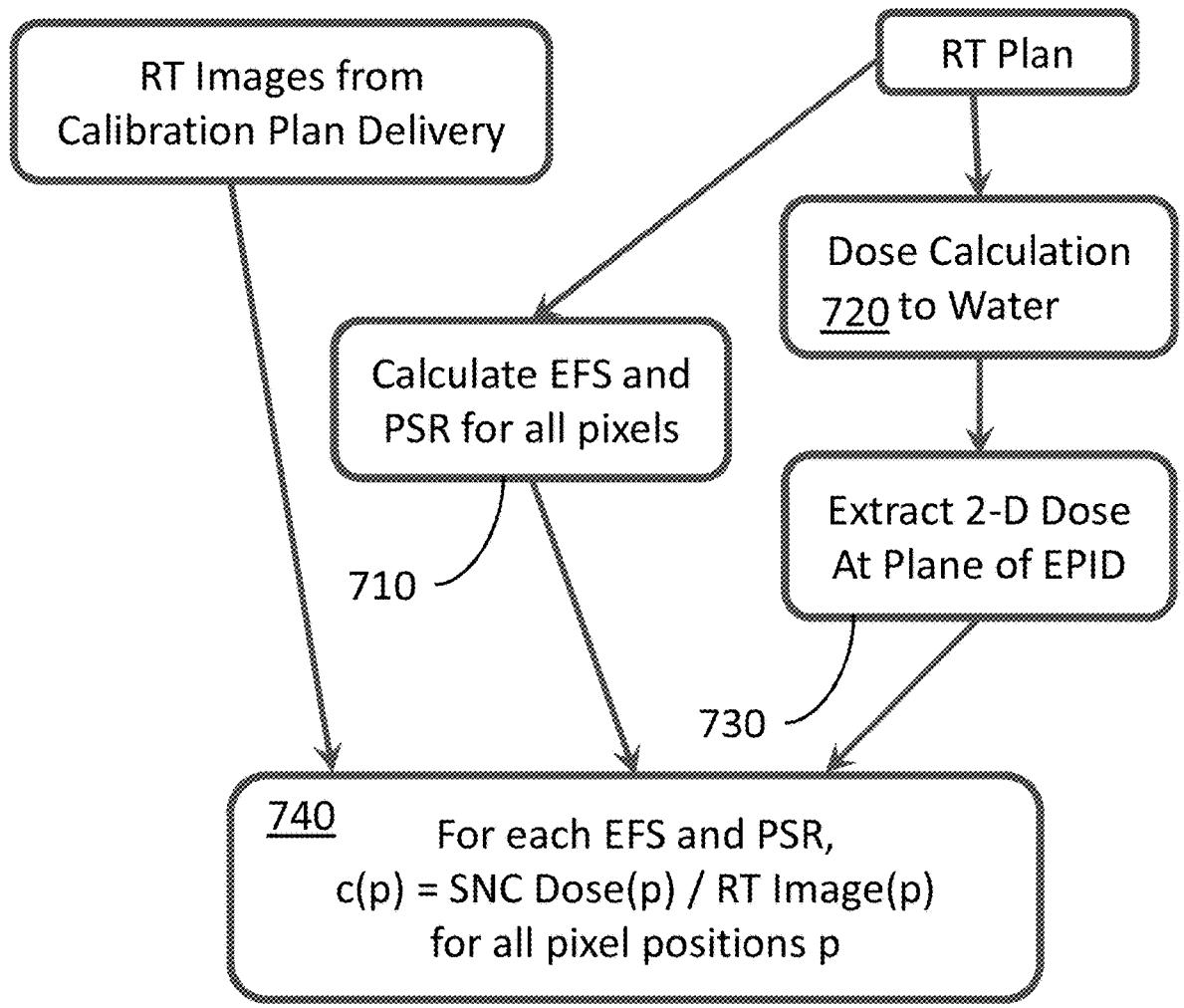
FIG. 7 is a process flow diagram illustrating a method of verifying a delivered radiation dose in accordance with certain aspects of the present disclosure.

FIG. 7 is a process flow diagram illustrating a method of verifying a delivered radiation dose in accordance with certain aspects of the present disclosure.

At 710, based on the treatment plan, for each pixel a number of effective field sizes and PSR can be calculated or specified for inclusion in the multidimensional conversion structure 530.

At 720, based on the treatment plan, a dose calculation can be generated with a dose calculation engine. The dose calculation can be based on the dose received by a water phantom.

At 730, a two dimensional dose map can be extracted from the dose calculation. The two dimensional dose map can correspond to the dose at a plane of the radiation detector.

At 740, for each effective field size and PSR, a conversion factor can be calculated and stored in the multidimensional conversion structure 530 for all pixel positions.

The present disclosure contemplates that the calculations disclosed in the embodiments herein may be performed in a number of ways, applying the same concepts taught herein, and that such calculations are equivalent to the embodiments disclosed.

The present disclosure also contemplates that any of the conversion factors calculated or determined herein can result from one or more mathematical operations, implemented by a physical processor. The operations can include, for example, addition, subtraction, multiplication, division, any combination thereof, applied to the images, maps, parameters, or other conversion factors described herein.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Specifically, and by way of example, although the headings refer to a "Technical Field," such claims should not be limited by the language chosen under this heading to describe the so-called technical field. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A method for implementation by at least one data processor for radiation therapy treatment verification, the method comprising:
   acquiring treatment plan information from a radiation therapy system;
   acquiring patient image data;
   acquiring transit image data received from an electronic portal imaging device during radiation therapy;
   dividing the treatment plan information into a plurality of segments;
   determining predicted segment image data utilizing a predicted image calculation algorithm and at least the patient image data, and the treatment plan information;
   determining a predicted integrated image through superposition of the predicted segment image data;
   determining measured segment responses from the transit image data utilizing the predicted segment image data and the predicted integrated image;
   converting the measured segment responses to measured segment doses; and
   comparing a measured dose map comprising a sum of the measured segment doses to a planned dose map based on the treatment plan information to assess radiation treatment delivery.

2. The method of claim 1, the comparing further comprising:
   transmitting, to a recipient device, a difference between the measured dose map and the planned dose map.

3. The method of claim 1, the converting comprising utilization of an effective field size calculator.

4. The method of claim 1, the converting comprising utilization of a ray tracer algorithm.

5. The method of claim 2, the comparing further comprising at least one of:
   displaying, at an electronic display, a report comprising the difference; and
   generating, at an electronic device, a warning based on the difference.

6. The method of claim 1, the converting comprising:
   accessing, from at least one database, a measurement of an output of a treatment beam, the patient image data, and a physical configuration of the radiation therapy system;
   generating a conversion factor based on the accessed measurement, the patient image data, and the physical configuration corresponding to a segment; and
   applying the conversion factor to the measured segment responses to generate the measured segment doses.

7. The method of claim 1, wherein the patient image data comprises three-dimensional images of patient anatomy.

8. The method of claim 1, wherein each of the plurality of segments correspond to a time window where the radiation treatment delivery of dose to a portion of a patient anatomy is substantially constant.

9. The method of claim 1, the converting comprising:
   executing a neural network to generate the predicted integrated image by weighting a predicted segment response contribution as part of an input layer of the neural network.

10. The method of claim 1, wherein the comparison of the measured dose map to the planned dose map comprises the comparison of a first sum of the measured segment doses to a second sum of the desired doses.

11. The method of claim 1, further comprising:
    generating an electronic warning at a display device based on the comparing of the measured dose map to the planned dose map, when a dose is outside of a predetermined dose limit.

12. The method of claim 1, the determining of the measured segment responses comprising:
    extracting a predicted response contribution based on the predicted segment image data and the predicted integrated image; and
    generating the measured segment response from the predicted response contribution and the transit data.

13. A computer program product comprising a non-transitory, machine-readable medium storing instructions which, when executed by at least one programmable processor, cause the at least one programmable processor to perform operations comprising:

acquiring treatment plan information from a radiation therapy system;

acquiring patient image data;

acquiring transit image data received from an electronic portal imaging device during radiation therapy;

dividing the treatment plan information into a plurality of segments; determining predicted segment image data utilizing a predicted image calculation algorithm and at least the patient image data, and the treatment plan information;

determining a predicted integrated image through superposition of the predicted segment image data;

determining measured segment responses from the transit image data utilizing the predicted segment image data and the predicted integrated image;

converting the measured segment responses to measured segment doses; and comparing the measured segment doses to desired doses to assess radiation treatment delivery.

14. A system comprising:

a radiation therapy system comprising:

an electronic portal imaging device; and a radiation source configured to generate a treatment beam that intersects the electronic portal imaging device;

at least one programmable processor; and a non-transitory machine-readable medium storing instructions which, when executed by the at least one programmable processor, cause the at least one programmable processor to perform operations comprising:

acquiring treatment plan information from the radiation therapy system;

acquiring patient image data;

acquiring transit image data received from the electronic portal imaging device during radiation therapy;

dividing the treatment plan information into a plurality of segments;

determining predicted segment image data utilizing a predicted image calculation algorithm and at least the patient image data, and the treatment plan information;

determining a predicted integrated image through superposition of the predicted segment image data;

determining measured segment responses from the transit image data utilizing the predicted segment image data and the predicted integrated image;

converting the measured segment responses to measured segment doses; and comparing the measured segment doses to desired doses to assess radiation treatment delivery.

\* \* \* \* \*